US010299871B2

(12) United States Patent
Zingaretti et al.

(10) Patent No.: US 10,299,871 B2
(45) Date of Patent: May 28, 2019

(54) AUTOMATED SYSTEM AND METHOD FOR HAIR REMOVAL

(71) Applicant: Restoration Robotics, Inc., San Jose, CA (US)

(72) Inventors: Gabriele Zingaretti, Capitola, CA (US); James W. McCollum, Coronado, CA (US); Mohan Bodduluri, Palo Alto, CA (US); Philip L. Gildenberg, Fort Meyers, FL (US); Donald E. Caddes, Menlo Park, CA (US)

(73) Assignee: Restoration Robotics, Inc., San Jose, CA (US)

( * ) Notice: Subject to any disclaimer, the term of this patent is extended or adjusted under 35 U.S.C. 154(b) by 233 days.

(21) Appl. No.: 15/216,005

(22) Filed: Jul. 21, 2016

(65) Prior Publication Data

US 2016/0324586 A1 Nov. 10, 2016

Related U.S. Application Data

(63) Continuation-in-part of application No. 14/177,462, filed on Feb. 11, 2014, now Pat. No. 9,526,581, which
(Continued)

(51) Int. Cl.
*A61B 17/00* (2006.01)
*A61B 17/34* (2006.01)
(Continued)

(52) U.S. Cl.
CPC ............ *A61B 34/32* (2016.02); *A61B 5/0077* (2013.01); *A61B 5/443* (2013.01); *A61B 5/448* (2013.01);
(Continued)

(58) Field of Classification Search
CPC ......... A61B 34/32; A61B 34/70; A61B 90/36; A61B 5/443; A61B 5/448; A61B 5/0077;
(Continued)

(56) References Cited

U.S. PATENT DOCUMENTS

| 2,667,879 A | 2/1954 | Mann |
| 3,867,942 A | 2/1975 | Bellantoni |

(Continued)

FOREIGN PATENT DOCUMENTS

| DE | 10249786 | 5/2004 |
| WO | WO 1998/025666 | 6/1998 |

(Continued)

OTHER PUBLICATIONS

Communication from EPC dated Jan. 5, 2009 in the Application No. 06804246.4, Applicant Restoration Robotics, Inc., Jan. 5, 2009, (3 pages).
(Continued)

*Primary Examiner* — Katrina M Stransky

(57) ABSTRACT

Automated systems and methods for removing hair from a body surface is provided. The methods and systems are semi- or fully automated. Some of the steps of the methods comprise determining a hair growth phase and selecting hair follicles for depilation based at least in part of the identified hair growth phase. The energy delivery device may be attached to the robotic arm and directed to align with the hair follicle to be depilated.

21 Claims, 14 Drawing Sheets

Related U.S. Application Data is a continuation of application No. 13/112,171, filed on May 20, 2011, now Pat. No. 8,690,894, which is a continuation of application No. 11/380,907, filed on Apr. 28, 2006, now Pat. No. 7,962,192.

(60) Provisional application No. 60/764,173, filed on Jan. 31, 2006, provisional application No. 60/753,602, filed on Dec. 22, 2005, provisional application No. 60/722,521, filed on Sep. 30, 2005.

(51) Int. Cl.
| | | |
|---|---|---|
| *A61B 34/00* | (2016.01) | |
| *A61B 34/10* | (2016.01) | |
| *A61B 34/20* | (2016.01) | |
| *A61B 34/30* | (2016.01) | |
| *A61B 34/32* | (2016.01) | |
| *A61B 17/3205* | (2006.01) | |
| *A61B 5/00* | (2006.01) | |
| *A61B 90/00* | (2016.01) | |
| *A61B 18/20* | (2006.01) | |
| *A61M 37/00* | (2006.01) | |
| *A61B 18/00* | (2006.01) | |

(52) U.S. Cl.
CPC ...... *A61B 5/4836* (2013.01); *A61B 17/32053* (2013.01); *A61B 17/3468* (2013.01); *A61B 18/203* (2013.01); *A61B 34/70* (2016.02); *A61B 90/36* (2016.02); *A61B 34/10* (2016.02); *A61B 34/30* (2016.02); *A61B 90/361* (2016.02); *A61B 2017/00057* (2013.01); *A61B 2017/00199* (2013.01); *A61B 2017/00752* (2013.01); *A61B 2018/00476* (2013.01); *A61B 2034/2057* (2016.02); *A61B 2090/064* (2016.02); *A61B 2090/371* (2016.02); *A61B 2218/005* (2013.01); *A61B 2576/02* (2013.01); *A61M 37/0076* (2013.01)

(58) Field of Classification Search
CPC .............. A61B 5/4836; A61B 5/0093; A61B 17/32053; A61B 2017/00752
See application file for complete search history.

(56) References Cited

U.S. PATENT DOCUMENTS

| | | |
|---|---|---|
| 4,004,592 A | 1/1977 | Yamada |
| 4,126,124 A | 11/1978 | Miller |
| 4,160,453 A | 7/1979 | Miller |
| 4,451,254 A | 5/1984 | Dinius |
| 4,476,864 A | 10/1984 | Tezel |
| 4,479,291 A | 10/1984 | Yamada |
| 4,598,311 A | 7/1986 | Bellina |
| 4,716,901 A | 1/1988 | Jackson |
| 4,751,927 A | 6/1988 | Yamada |
| 4,768,517 A | 9/1988 | Joachim |
| 4,807,163 A | 2/1989 | Gibbons |
| 4,969,903 A | 11/1990 | Valle |
| 4,980,971 A | 1/1991 | Bartschat |
| 5,036,860 A | 8/1991 | Leigh |
| 5,050,608 A | 9/1991 | Watanabe |
| 5,078,140 A | 1/1992 | Kwoh |
| 5,183,053 A | 2/1993 | Yeh |
| 5,207,671 A | 5/1993 | Franken |
| 5,230,623 A | 7/1993 | Guthrie |
| 5,251,127 A | 10/1993 | Raab |
| 5,331,472 A | 7/1994 | Rassman |
| 5,395,368 A | 3/1995 | Ellman |
| 5,417,683 A | 5/1995 | Shiao |
| 5,439,475 A | 8/1995 | Bennett |
| 5,449,370 A | 9/1995 | Vaitekunas |
| 5,483,961 A | 1/1996 | Kelly |
| 5,490,850 A | 2/1996 | Ellman |
| 5,562,613 A | 10/1996 | Kaldany |
| 5,578,054 A | 11/1996 | Arnold |
| 5,584,841 A | 12/1996 | Rassman |
| 5,584,851 A | 12/1996 | Banuchi |
| 5,611,810 A | 3/1997 | Arnold |
| 5,611,811 A | 3/1997 | Goldberg |
| 5,662,661 A | 9/1997 | Boudjema |
| 5,693,064 A | 12/1997 | Arnold |
| 5,733,278 A | 3/1998 | Slatkine |
| 5,749,362 A | 5/1998 | Funda |
| 5,782,843 A | 7/1998 | Aasberg |
| 5,782,851 A | 7/1998 | Rassman |
| 5,782,853 A | 7/1998 | Zeevi |
| 5,792,163 A | 8/1998 | Hitzig |
| 5,792,169 A | 8/1998 | Markman |
| 5,817,105 A | 10/1998 | Van Der Brug |
| 5,817,120 A | 10/1998 | Rassman |
| 5,827,217 A | 10/1998 | Silver |
| 5,827,297 A | 10/1998 | Boudjema |
| 5,836,938 A | 11/1998 | Slatkine |
| 5,858,019 A | 1/1999 | Ashraf |
| 5,865,744 A | 2/1999 | Lemelson |
| 5,873,888 A | 2/1999 | Costanzo |
| 5,893,853 A | 4/1999 | Arnold |
| 5,895,403 A | 4/1999 | Collinsworth |
| 5,899,916 A | 5/1999 | Casparian |
| 5,901,199 A | 5/1999 | Murphy |
| 5,951,572 A | 9/1999 | Markman |
| 5,961,529 A | 10/1999 | Arnold |
| 5,984,915 A | 11/1999 | Loeb |
| 5,984,936 A | 11/1999 | Mangubat |
| 5,989,273 A | 11/1999 | Arnold |
| 5,989,279 A | 11/1999 | Rassman |
| 5,997,550 A | 12/1999 | Russell |
| 6,013,087 A | 1/2000 | Adams |
| 6,027,512 A | 2/2000 | Bridges |
| 6,056,736 A | 5/2000 | Markman |
| 6,059,807 A | 5/2000 | Boudjema |
| 6,110,189 A | 8/2000 | Markman |
| 6,120,521 A | 9/2000 | Casparian |
| 6,162,212 A * | 12/2000 | Kreindel ............ A61B 18/203 606/131 |
| 6,228,075 B1 | 5/2001 | Furumoto |
| 6,341,831 B1 | 1/2002 | Weber |
| 6,445,943 B1 | 9/2002 | Ferre |
| 6,461,369 B1 | 10/2002 | Kim |
| 6,484,049 B1 | 11/2002 | Seeley |
| 6,547,782 B1 | 4/2003 | Taylor |
| 6,554,825 B1 | 4/2003 | Murray |
| 6,572,625 B1 | 6/2003 | Rassman |
| 6,585,746 B2 | 7/2003 | Gildenberg |
| 6,632,218 B1 | 10/2003 | Furumoto |
| 6,694,167 B1 | 2/2004 | Ferre |
| 6,717,102 B2 | 4/2004 | Neev |
| 6,917,702 B2 | 7/2005 | Beardsley |
| 6,973,931 B1 | 12/2005 | King |
| 7,083,611 B2 | 8/2006 | Lemchen |
| 7,175,617 B2 | 2/2007 | Jay |
| 7,217,266 B2 | 5/2007 | Anderson |
| 7,277,120 B2 | 10/2007 | Gere |
| 7,553,308 B2 | 6/2009 | Jay |
| 7,967,016 B2 | 6/2011 | Anderson |
| 8,690,894 B2 | 4/2014 | Bodduluri et al. |
| 9,364,684 B2 | 6/2016 | Poran |
| 2001/0034534 A1 | 10/2001 | Transue |
| 2002/0103500 A1 | 8/2002 | Gildenberg |
| 2002/0133149 A1 | 9/2002 | Bessette |
| 2002/0151784 A1 | 10/2002 | Mizoguchi |
| 2003/0040766 A1 | 2/2003 | Werner |
| 2003/0060810 A1 | 3/2003 | Syrowicz |
| 2003/0097144 A1 | 5/2003 | Lee |
| 2003/0181801 A1 | 9/2003 | Lasser |
| 2003/0181936 A1 | 9/2003 | Trautman |
| 2004/0034282 A1 | 2/2004 | Quaid, III |
| 2004/0092924 A1 | 5/2004 | Vasa |
| 2004/0116942 A1 | 6/2004 | Feller |
| 2004/0162505 A1 | 8/2004 | Kaplan |

(56) References Cited

U.S. PATENT DOCUMENTS

| | | | |
|---|---|---|---|
| 2004/0193203 A1 | 9/2004 | Pak | |
| 2004/0204700 A1 | 10/2004 | Weaver | |
| 2004/0220589 A1 | 11/2004 | Feller | |
| 2004/0225314 A1 | 11/2004 | Fukuyama | |
| 2004/0243147 A1 | 12/2004 | Lipow | |
| 2006/0079816 A1 | 4/2006 | Barthe | |
| 2007/0038236 A1 | 2/2007 | Cohen | |
| 2007/0106306 A1* | 5/2007 | Bodduluri | A61B 17/32053 606/133 |
| 2007/0255293 A1 | 11/2007 | Corre | |
| 2007/0293884 A9 | 12/2007 | Cole | |
| 2008/0002809 A1 | 1/2008 | Bodduluri | |
| 2008/0154247 A1* | 6/2008 | Dallarosa | A61B 18/203 606/3 |
| 2008/0242990 A1 | 10/2008 | Zanelli | |
| 2008/0247637 A1 | 10/2008 | Gildenberg | |
| 2009/0099559 A1 | 4/2009 | Dhadwal | |
| 2009/0230269 A1 | 9/2009 | Dallarosa | |
| 2010/0125287 A1 | 5/2010 | Cole | |
| 2010/0228163 A1* | 9/2010 | Zanelli | A61N 7/02 601/3 |
| 2013/0237973 A1 | 9/2013 | Kim | |
| 2016/0193035 A1* | 7/2016 | Silva Ramos | A61B 34/30 606/130 |
| 2016/0324586 A1 | 11/2016 | Zingaretti et al. | |

FOREIGN PATENT DOCUMENTS

| | | |
|---|---|---|
| WO | 9927863 A1 | 6/1999 |
| WO | WO 2006/021040 | 3/2006 |

OTHER PUBLICATIONS

Non-Final Office Action dated Jan. 16, 2013, in relation to commonly assigned U.S. Appl. No. 13/112,171, Jan. 16, 2013, (15 pages).

Office Action dated Dec. 11, 2008, for U.S. Appl. No. 11/380,907, filed Apr. 28, 2006, Applicant Restoration Robotics, Inc.

International Search Report and Written Opinion, PCT/US2017/043038, Nov. 2, 2017.

Website, http://www.medicamat.com/materiel/hair-transplant/omnigraft.html?L=1, Medicamat, Medical and Surgical Devices, Cosmetic Products, Hair Transplant/Omnigraft, accessed on Aug. 8, 2007, (1 page).

Website, http://www.medicamat.com/materiel/hair-transplant/punchhairmatic.html?L=1, Medicamat, Medical and Surgical Devices, Cosmetic Products, Hair Transplant/Punch Hair Matic, accessed on Aug. 8, 2007, (1 page).

Website, http://www.medicamat.com/materiel/hair-transplant/omnigraft/case-study.html?L=1, Omnigraft, Medicamat, Medical and Surgical Devices, Cosmetic Products, Hair Transplant/Omnigraft/Case Study, accessed on Aug. 8, 2007, (4 pages).

Website, http://www.medicamat.com/materiel/hair-transplant/punchhairmatic/case-study.html?L=1, Medicamat, Medical and Surgical Devices, Cosmetic Products, Hair Transplant/Punch Hair Matic/Case Study, Website, http://www.medicamat.com/materiel/hair-tr, (3 pages).

Annex to form PCT/ISA/206, Communication Relating to the Results of the Partial International Search, attached to PCT Invitation to Pay Additional Fees, PCT/ISA/206, for PCT/US2006/0038002, Applicant Restoration Robotics, Inc., dated Jan. 25, 2007.

"Automated Hair Restoration System, OmniGraft", Brochure—Medicamat, (4 pages).

PCT International Search Report for PCT/US2006/0038002, Applicant Restoration Robotics, Inc., forms PCT/ISA/210 and 220, dated Apr. 11, 2007, (7 pages).

PCT Written Opinion of the International Search Report Authority for PCT/US2006/0038002, Applicant Restoration Robotics, Inc., Form PCT/ISA/237, dated Apr. 11, 2007 (7 pages).

"Punch-Hair-Matic A New Robot to Fight Baldness", Brochure—Medicamat (3 pages).

Forsyth, et al., "Computer Vision, A Modern Approach", Cover page, publication page, and Chapters 10 & 11, Pearson Education, Inc., 2003, pp. 215-250.

Harris, "New Methodology and Instrumentation for Follicular Unit Extraction: Lower Follicle Transection Rates and Expanded Patient Candidacy", Dermatol Surg 32, Jan. 2006.

Inaba, et al., "Androgenetic Alopecia, Modern Concepts of Pathogenesis and Treatment, 29. Operative Treatment for Androgenetic Alopecia.", 1996, pp. 238-244, 309 (9 pages).

Jain, et al., "Machine Vision", Cover page, publication page, and Chapters 11 & 12. McGraw-Hill, Inc., 1995, pp. 289-364.

Johannes, "Lasers Aim to Stimulate a Hair-Growth Spurt", Wall Street Journal.

Konolige, et al., "SRI Small Vision System", SRI International—User's Manual Software Version 3.2g, Nov. 2004, (86 pages).

Lanfranco, et al., "Robotic Surgery : A Current Perspective", Annals of Surgery, vol. 239, No. 1,, Jan. 2004, 14-21 pages.

Lumenis, "VersaPulse PowerSuite Lasers", Product Brochure.

Mandt, et al., "Epilation Today: Physiology of the Hair Follicle and Clinical Photo-Epilation", Journal of Investigative Dermatology Symposium Proceedings (2005) 10, 2005, pp. 271-274.

Marshall, "Semiconductor-Based Lasers in Medicine", Lasers and Electro-Optics Society Annual Meeting, 1998. LEOS '98. vol. 2, Dec. 1-4, 1998 p. 339, Dec. 1998, p. 339.

Riordan, "Implanting Hair is Tedious, Exacting Work—the Perfect Work for a Robot", The New York Times,, Sep. 15, 2003, (1 page).

Sadick, "Laser Hair Removal", Facial Plast Surg Clin N Am 12 (2004), 2005, pp. 191-200.

Woodfill, et al., "The Tyzx DeapSea G2 Vision System, A Taskable, Embedded Stereo Camera", Proceedings of the IEEE Computer Society Workshop on Embedded Computer Vision, Conference on Computer Vision and Pattern Recognition, Jun. 2006, 5 pages.

Woodfill, et al., "Tyzx DeepSea High Speed Stereo Vision System", Proceedings of the IEEE Computer Society Workshop on Real Time 3-D Sensors and Their Use, Conference on Computer Vision and Pattern Recognition, (Washington, D.C.), Jun. 2004, 5 pages.

Zenzie, et al., "Super Long Pulse Hair Removal", Laser and Electro-Optics Society 2000 Annual Meeting, LEOS 2000. 13th Annual Meeting.IEEE vol. 1, Nov. 13-16, 2000, Nov. 2000, pp. 208-209.

* cited by examiner

AUTOMATED SYSTEM AND METHOD FOR HAIR REMOVAL

RELATED APPLICATION DATA

The present application is a continuation-in-part of co-pending U.S. patent application Ser. No. 14/177,462 entitled "Automated System and Method for Harvesting or Implanting Follicular Units", filed Feb. 11, 2014, which is a continuation of U.S. patent application Ser. No. 13/112,171, entitled "Automated System for Harvesting or Implanting Follicular Units", filed May 20, 2011, now U.S. Pat. No. 8,690,894, which is a continuation of U.S. patent application Ser. No. 11/380,907, entitled "Systems and Methods for Aligning a Tool with a Desired Location or Object", filed Apr. 28, 2006, now U.S. Pat. No. 7,962,192 issued Jun. 14, 2011, which claims the benefit under 35 U.S.C. § 119 to U.S. provisional patent application Ser. No. 60/722,521, filed Sep. 30, 2005, 60/753,602, filed Dec. 22, 2005, and 60/764,173, filed Jan. 31, 2006. The foregoing applications are all hereby incorporated by reference into the present application in their entirety.

FIELD OF INVENTION

This invention relates generally to an image-guided robotic system for performing precision diagnostic and therapeutic medical procedures, and more specifically, to automated (e.g., robotic) systems and methods for controlled application of energy into or through a body surface to targeted cutaneous and subcutaneous tissue regions for hair and skin treatment procedures, including hair removal.

BACKGROUND

Numerous procedures are currently performed, or are under consideration, for both therapeutic and cosmetic (both aesthetic and reconstructive) purposes, including hair transplantation, hair removal, therapeutic and cosmetic injections, tattoo placement and removal, and various procedures in which energy is applied to a targeted area of a patient's body. For therapeutic or cosmetic skin and hair treatments, the energy is typically applied to cutaneous tissue regions, but may penetrate to some subcutaneous tissue regions. For example, lasers are currently used for numerous skin and hair procedures, such as hair removal, laser skin resurfacing for treating wrinkles, tattoo removal, nonablative skin treatment, and more. Generally, these procedures involve using a hand-held laser applicator. The type of laser utilized, and the physiological and/or chemical process involved varies depending on the type of procedure. However, the current systems for therapeutic and cosmetic application of laser and RF energy utilize manual techniques for positioning, aiming and operating the lasers. Treatments utilizing these manual techniques are often long and tedious. Moreover, because the laser or RF device is positioned and operated manually, the efficacy of such procedures may be operator dependent and thus, inconsistent.

U.S. Pat. No. 6,585,746 discloses a hair transplantation system utilizing a robot, including a robotic arm and a hair follicle introducer associated with the robotic arm. There is a need for further improvements in robotic hair transplantation as well as development of an automated (e.g., robotic) apparatus and method for performing other cosmetic, diagnostic and therapeutic procedures, including those involving the application of energy to a treatment area of a patient's body, especially procedures that require a precise location targeting and a large number of movements of the tool, such as energy delivery device.

SUMMARY

In accordance with a general aspect of the inventions disclosed herein, an automated system, such as an image-guided robotics system, is employed for performing precisely controlled diagnostic and therapeutic medical procedures, such as (by way of non-limiting examples) hair removal and/or transplantation, repetitive needle injections (e.g., for delivery of collagen fillers, melanocyte, tattoo ink), tattoo or mole removal, application of laser or radio frequency (RF) energy, cryogenic therapy (e.g., for mole or wart removal), patterned micro-tissue removal (e.g., as an alternative to a conventional "face lift" procedure), and any other procedure currently performed using human-controlled devices.

According to some embodiments, an automated system may also be employed for performing diagnostic evaluations, such as, e.g., obtaining precision image data for skin cancer screening, and performing ultrasound diagnostics. In various embodiments, the robotics system generally includes a robotic arm controlled by a system controller, an end-effecter assembly coupled to a distal (tool) end of the robotic arm, and an image acquisition system, including one or more high speed cameras coupled to the end-effecter assembly for acquiring images that are processed for providing control signals for movement of the robotic arm using a "visual-servoing" process.

In accordance with some embodiments of the invention, an automated system for harvesting or implanting follicular units is provided, the system including a moveable arm, a tool mounted on the moveable arm, one or more cameras mounted on the moveable arm, a processor configured to receive and process images acquired by the one or more cameras, and a controller operatively associated with the processor and configured to position the moveable arm based, at least in part, on processed images acquired by the one or more cameras, wherein the moveable arm is positionable such that the tool may be positioned at a desired orientation relative to an adjacent body surface.

By way of non-limiting example, the automated system may be a robotic system, wherein the moveable arm is a robotic arm, and wherein the processor and controller may be configured for positioning the tool by visual servoing of the robotic arm. In some embodiments, a single camera may be employed, wherein the processor is configured to register a reference coordinate system of the camera with a tool frame reference coordinate system of the robotic arm. For example, the processor may register the camera reference coordinate system with the tool frame reference coordinate system based on images of a fixed calibration target acquired as the robotic arm is moved along one or more axes of the tool frame reference coordinate system. By way of another example, a pair of cameras may be mounted to the robotic arm, wherein the processor is configured to register respective reference coordinate systems of the cameras with each other and with a tool frame reference coordinate system of the robotic arm. Again, the processor may register the respective camera reference coordinate systems with the tool frame reference coordinate system based on images of a fixed calibration target acquired as the robotic arm is moved along one or more axes of the tool frame reference coordinate system. By way of yet another example, the one or more cameras comprises respective first and second pairs of cameras mounted to the robotic arm, the first pair focused to acquire images of a first field of view, and the second pair focused to acquire images of a second field of view substantially narrower than the first field of view. In this embodiment, the processor may be configured to register respective reference coordinate systems of the first and second pairs of cameras with each other and with a tool frame reference coordinate system of the robotic arm. Again, the processor may register the respective camera reference coordinate systems with the tool frame reference coordinate system based on images of a fixed calibration target acquired as the robotic arm is moved along one or more axes of the tool frame reference coordinate system.

In various embodiments, the processor may be configured to identify approximate physical boundaries of a follicular unit in an image acquired by the one or more cameras. For example, the processor may be configured for identifying approximate physical boundaries of a follicular unit captured in an acquired image, including a subcutaneous base region embedded in the body surface and a distal tip region extending away from the body surface, wherein the images include subcutaneous images. In yet another embodiment, an air jet is provided on the moveable arm for directing an air stream at the body surface. In yet another embodiment, a user interface is provided for a user to input instructions to one or both of the processor and controller regarding one or more of a location, position, orientation, and depth of a hair follicle or follicular unit to be removed or implanted.

In accordance with further embodiments, an automated system for removing, destroying, harvesting or implanting follicular units includes a moveable arm, a tool mounted on the moveable arm, a pair of cameras, a processor configured to receive and process images acquired by the cameras, wherein the processor is configured to register respective reference coordinate systems of the cameras with each other, and a controller operatively associated with the processor and configured to position the moveable arm based, at least in part, on processed images acquired by the cameras, wherein the moveable arm is positionable such that the tool may be positioned at a desired orientation relative to an adjacent body surface. By way of non-limiting example, the automated system may be a robotic system, wherein the moveable arm is a robotic arm, and the processor is further configured to register the respective camera reference coordinate systems with a tool frame reference coordinate system of the robotic arm. In such embodiment, the processor and controller may be configured for positioning the tool by visual servoing of the robotic arm.

In accordance with yet another aspect of the present disclosure, a method for aligning a tool positioned on a moveable arm of an automated system with a location or an object of interest on a skin is provided. The method comprising: determining a fixed relationship between the tool positioned on the moveable arm and at least two cameras positioned on the movable arm, wherein the tool is capable of manipulating tissue; selecting a location or an object of interest on a skin; identifying position offsets of the location or the object of interest from the at least two cameras; automatically moving the moveable arm to align the tool with the location or the object of interest on the skin based, at least in part, on the identified offsets and on maintaining while aligning the tool the fixed relationship between the at least two cameras and the tool. For example, the automated system may be a robotic system, wherein the moveable arm is a robotic arm, and the processor may be further configured to register the respective camera reference coordinate systems with a tool frame reference coordinate system of the robotic arm. In some embodiments, where the object of interest is hair, automatically moving the movable arm to align the tool with the hair comprises aligning a longitudinal axis of the tool with either an elongated axis of the hair above the skin or with an anticipated axis of the hair below the skin, depending, for example, upon the emergence angle of the hair with respect to the body surface. In some embodiments, the method for orienting a tool comprises determining an emergence angle of a hair follicle of interest, choosing a minimal approach angle of the tool, comparing the emergence angle of the hair follicle of interest with the minimum approach angle of the tool, and orienting the tool relative to the hair follicle of interest based on a result of the comparison of the emergence angle of the hair follicle of interest with the minimum approach angle of the tool. Orienting the tool may comprise automatically moving a robotic arm to which the tool is operatively connected, or actuating various motors and mechanisms to change position/orientation of the tool, or any combination of the above. Choosing the minimum approach angle of the tool may be based at least in part on an average or mean emergence angle of a plurality of hairs in an area. In other embodiments, the method of orienting or aligning a tool may comprise determining an emergence angle of a hair follicle of interest, choosing a predetermined offset angle, and orienting the tool relative to the hair follicle of interest based on the determined emergence angle of the hair follicle of interest and the predetermined offset angle. The predetermined offset angle may comprise an angle of between 0 and 45 degrees, for example, in the range of 10-20 degrees.

An automated system or apparatus comprising a processor configured or programmed to implement the above-described methodology is also provided. Such processor may comprise one or more modules for executing instructions for performing various steps of the disclosed methods. The automated system may also comprise an imaging device and an image processor, the image processor may be a separate processor or a part of the same processor that controls implementation of the various steps of the method.

According to yet another aspect of the present disclosure, automated (e.g. robotic) systems and methods are provided for controlled application of energy into or through skin layers of a patient to targeted tissue regions (a "treatment location") for hair and skin treatment procedures. A treatment location may comprise one or more of the following: skin, tissue within skin layers, hair, and/or the subcutaneous fat layer proximately beneath the skin. In some embodiments an automated treatment system comprises an energy delivery device positioned on a movable arm (e.g., robotic arm). The system also comprises a processor and/or controller configured to control movement of the movable arm, and optionally also control movements/operation of the tool. The operation of the tool may be controlled by a separate processor/controller and/or by various mechanisms. The system may also comprise one or more imaging devices, and the processor and/or controller may direct movement of the movable arm (and optionally, the tool) at least in part based on the images acquired by the one or more imaging devices (e.g. cameras). The cameras may be configured to provide information regarding the region of interest, including information regarding skin and/or hair in the region of interest, and the location of the energy delivery device relative to the treatment location. The cameras may be positioned on the movable arm, on a different arm, or on some other structure of the system. Alternatively, the imaging device(s) may be a separate device, and the automated treatment system may comprise an interface configured to receive the images obtained from such separate imaging device(s).

The energy delivery device may be any suitable device for applying therapeutic or cosmetic energy to cutaneous and subcutaneous tissue regions, including without limitation any of the lasers and light sources described below. The energy delivery device may be chosen to transmit energy in any desired form. By way of non-limiting example, the energy can be: electromagnetic energy including without limitation radiofrequency, visible light, microwave, x-ray, infra-red, etc. using a laser or other energy source; ultrasound; electrical; or magnetic. The energy delivery device may be integrated on the movable arm. In some embodiments the power unit for the energy delivery device may also be integrated with the energy delivery device on the movable arm, or alternatively, it may be located other than on the movable arm, and the energy may be directed from the power unit to the energy delivery device attached to the movable arm. For example, a laser power unit may be located off of the robotic arm and a fiber optic cable may be used to direct the laser beam (the energy) to the energy delivery device on the robotic arm, such as a lens or other energy delivery device attached to the robotic arm.

A user interface is operably coupled to the processor and/or controller and is configured to display the images taken by the cameras, or information/images created as a result of processing the images taken by the cameras. The user interface may be further configured to allow the user to input parameters and/or instructions for the treatment, such as the desired area of the treatment location(s), the type, intensity or duration of the energy device utilized for the treatment, spot size, and/or fluence, among other possible parameters. The user interface may also be configured to display to the user one or more of the parameters/instructions that may be automatically suggested by the system, such as robotic system 25, including without limitation: treatment location(s), the type, intensity or duration of the energy device utilized for the treatment, spot size, and/or fluence, and allow the user to modify, accept or delete one or more of the automatically suggested parameters.

According to yet another aspect, a method of hair depilation using an automated system is provided. The method comprising automatically identifying in an image acquired by an imaging device, a location and orientation of unwanted hair follicles in a region of a body surface. The method also comprises one or both of the following steps: automatically measuring and assigning a skin pigmentation value in the region of the body surface with the identified unwanted hair follicles and automatically measuring and assigning a hair pigmentation value for some or all of the identified unwanted hair follicles. Based on one or both of the assigned skin pigmentation value and the assigned hair pigmentation value of one or more identified unwanted hair follicles, an energy delivery device is automatically selected from a plurality of energy delivery devices operatively connected to the automated system; and based on the identified location and orientation of one of the one or more identified hair follicles, the selected energy delivery device is automatically directed to align with the one or more identified hair follicles. Automatically aligning may comprise automatically aligning with a general direction of the hair shaft portion of the one or more identified hair follicles, and in some embodiments automatically aligning may comprise automatically aligning with a general direction of the hair shaft portion below a skin surface. In some embodiments, the method may further comprise operating the energy delivery device to depilate the one of the one or more identified hair follicles. Identification of one or more hair follicles may comprise identifying hair follicles in an anagen hair growth phase, which may comprise identifying hair caliber.

An automated system or apparatus comprising a processor configured or programmed to implement the above-described methodology is also provided. Such processor may comprise one or more modules for executing instructions for performing various steps of the disclosed methods. The automated system may also comprise an interface, an imaging device, a robotic arm and a tool coupled to the robotic arm. The tool may comprise one or more energy delivery devices that can be selectively activated by a user or automatically by the system. The apparatus may further comprise an air jet configured for directing an air stream at a targeted hair follicle, and a processor may comprise instructions for automatically directing the air jet to align with the energy delivery device and activating the air jet simultaneously with activation of the energy delivery device. In further embodiments, the processor is configured to determine a time for which the selected energy delivery device is to be operated (continuously or pulsed), based on a pigmentation of skin, and also based on one or more of the following: a pigmentation of an identified anagen hair and a caliber of an identified anagen hair.

According to a further aspect, a method of hair depilation using an automated system is provided. The method comprises automatically identifying in an image acquired by an imaging device a location and orientation of one or more unwanted hair follicles in a region of a body surface and automatically determining which of the one or more hair follicles are in an anagen hair growth phase. In some embodiments, the method may optionally further comprise one or both of the following: automatically measuring and assigning a hair pigmentation value for some or all of the identified unwanted hair follicles and automatically measuring and assigning a skin pigmentation value in the region of the body surface with the identified unwanted hair follicles. Based on the identified hair follicles in the anagen hair growth phase (and optionally, based on the assigned hair pigmentation value and/or skin pigmentation value), one or more hair follicles are selected for depilation. According to the proposed method, an energy delivery device is selected and directed to be positioned and oriented relative to the one or more hair follicles selected for depilation. In some embodiments, the step of determining which of the one or more hair follicles is in anagen hair growth phase comprises determining a caliber of at least a portion of the hair shaft above the skin. In some embodiments, the method comprises directing a stream of air at the hair follicle being depilated. In other embodiments directing the energy delivery device to be positioned and oriented relative to the one or more hair follicles comprises aligning the energy delivery device with a general direction of the hair shaft, aligning the energy delivery device with a general direction of a portion of the hair shaft beneath a skin, or orienting the energy delivery device at an offset angle to the general direction of the hair shaft of the one of the hair follicles above the skin surface.

An automated system or apparatus comprising a processor configured or programmed to implement the above-described methodology is also provided.

Accordingly, the automated treatment systems and methods of the present disclosure not only provide for more standard and consistent application of treatment energy as compared to current manual techniques, but also make such procedures more precise, efficient, shorter in duration, and potentially reduce pain and possibility of damage to the surrounding tissue.

Other and further objects and advantages of the invention will become apparent from the following detailed description when read in view of the accompanying figures.

BRIEF DESCRIPTION OF THE DRAWINGS

The invention is illustrated by way of example and not limitation in the figures of the accompanying drawings, in which like references indicate similar elements, and in which.

DETAILED DESCRIPTION OF THE ILLUSTRATED EMBODIMENTS

Figure 1:
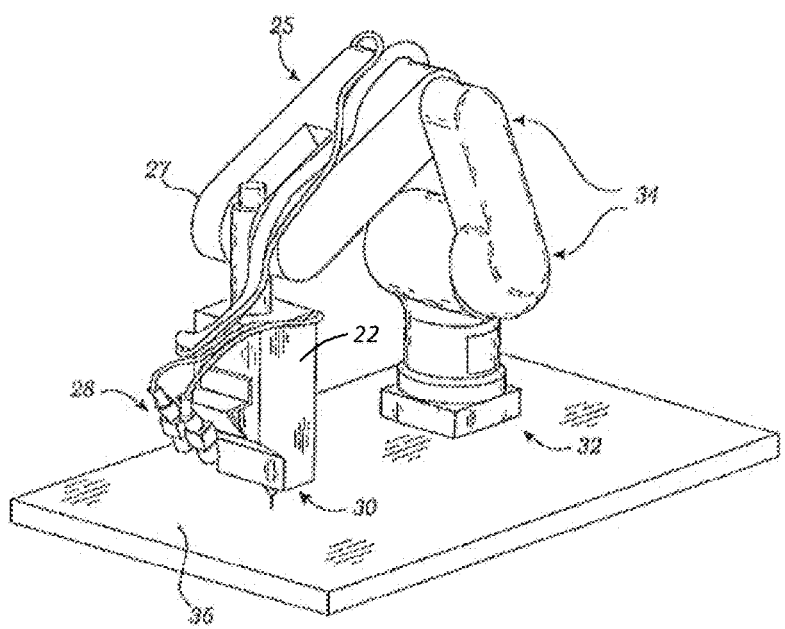
FIG. 1 is a representation of an embodiment of an image-guided robotics system, including a robotic arm for positioning and orienting an end-effecter tool or a tool at targeted locations on the skin surface of a patient.

FIG. 1 depicts an image-guided robotics system 25, including a programmable robotic arm 27 of a type manufactured and distributed by Adept Technology, Inc. (www.adept.com). Another source of robotic arm assemblies suitable for embodiments of the invention are manufactured and distributed by Kuka Robot Group (www.kuka.com). The robotic arm 27 provides precisely controlled movement of a distal end plate (not seen in FIG. 1) in six degrees of freedom (x, y, z, ω, ρ, r), as is well-known in the art. Such movement of the distal plate is provided with a high degree of repeatability and accuracy (e.g., to 20 microns) by respective motors and encoders located in respective arm joints 34 of the robotic arm 27.

Figure 2:
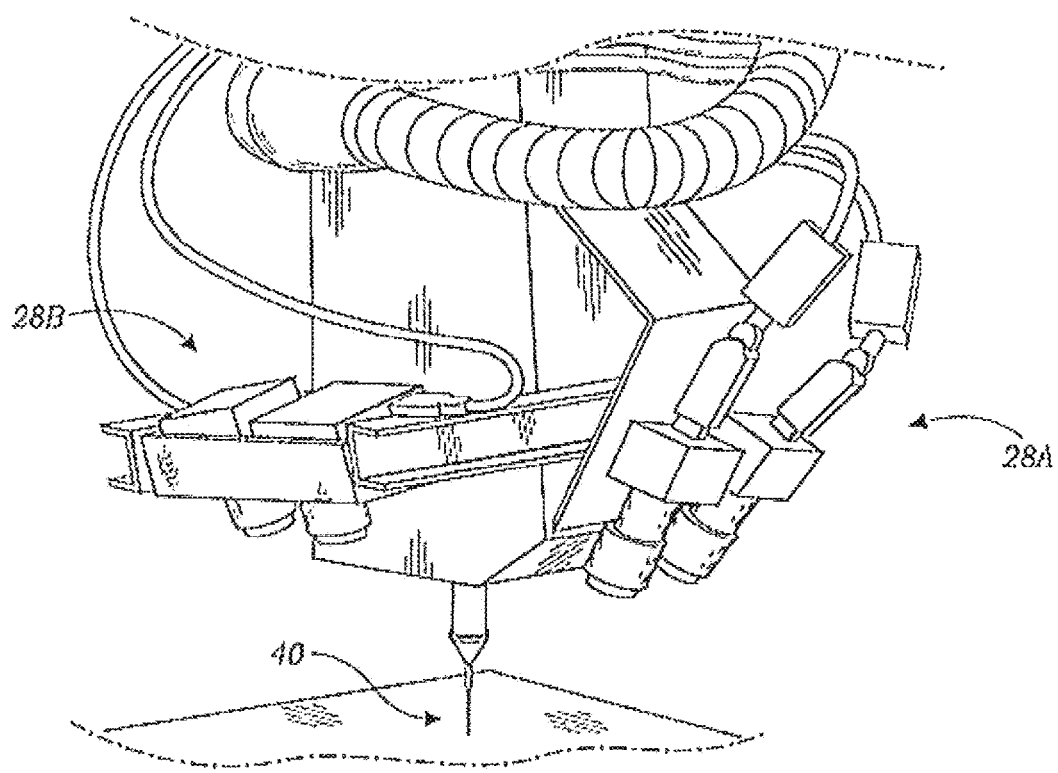
FIG. 2 is a representation showing first and second stereo camera pairs secured to the robotic arm of FIG. 1, and used to capture image data from multiple fields-of-view for guiding movement of the robotic arm and an attached end-effecter tool assembly.
Figure 3:
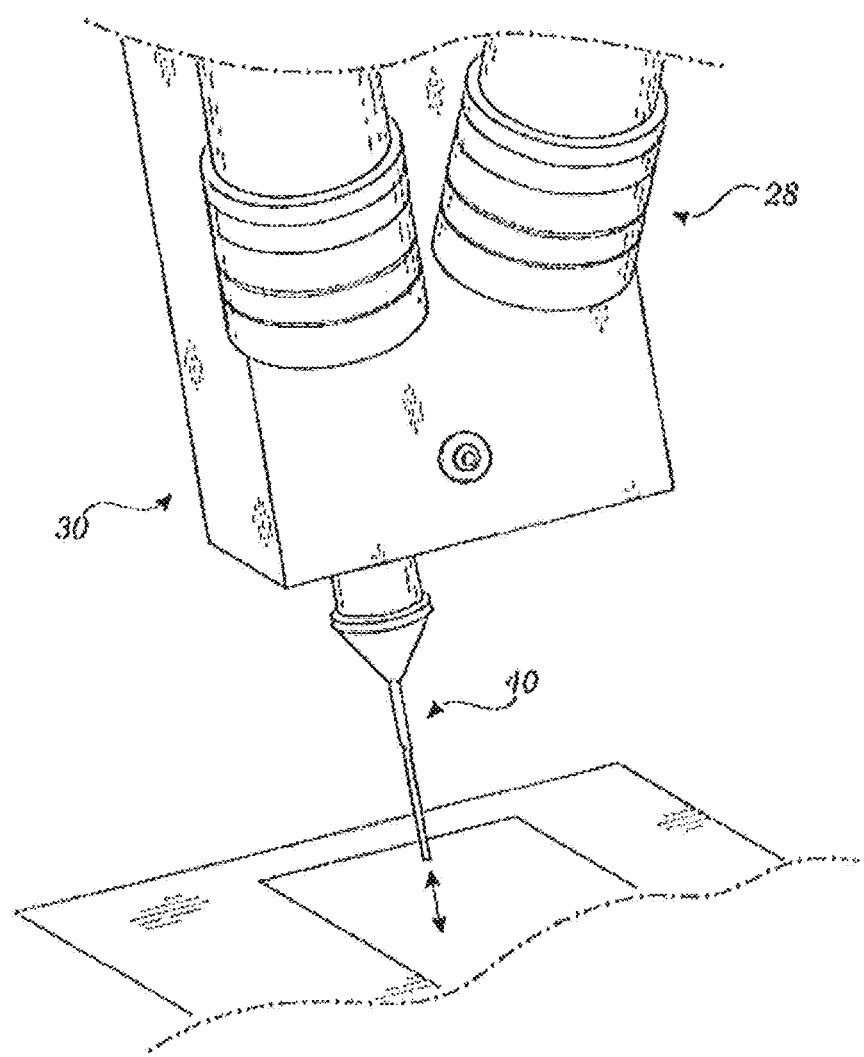
FIG. 3 is a close-up photograph of the system of FIG. 2, more clearly showing the end-effecter tool.

A variety of different end-effecter tools and/or assemblies may be attached to the distal end plate on the robotic arm 27 for performing various procedures on a human or animal patient. By way of example, the end-effecter assembly or tool assembly 30 shown in FIGS. 1-3 is designed for the harvesting and implantation of hair follicles from/in a human scalp. It will be appreciated that embodiments of the invention will employ many different types of end-effecter tools, such as a tool 40 shown in FIG. 2, and assemblies for performing diagnostic and therapeutic medical procedures that take advantage of the ability of the robotic arm 27 to rapidly and precisely position the respective tool (e.g., needle, laser) or assembly at desired locations at the skin surface of a patient. It will be appreciated that the end-effecter assemblies may themselves include moving, controllable parts. By way of example, one end-effecter assembly comprises a reciprocating needle used for delivering precisely targeted, repetitive injections through the dermis.

Figure 2A:
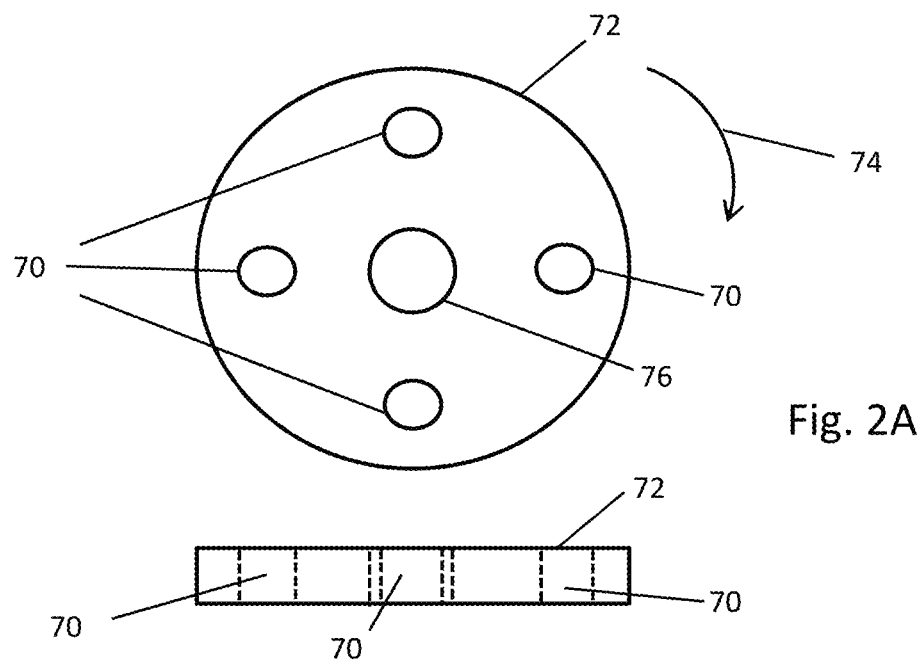
FIGS. 2A and 2B illustrate some alternative examples of how multiple energy delivery devices may be accommodated in a housing of a robotics system according to the present disclosure.
Figure 2B:
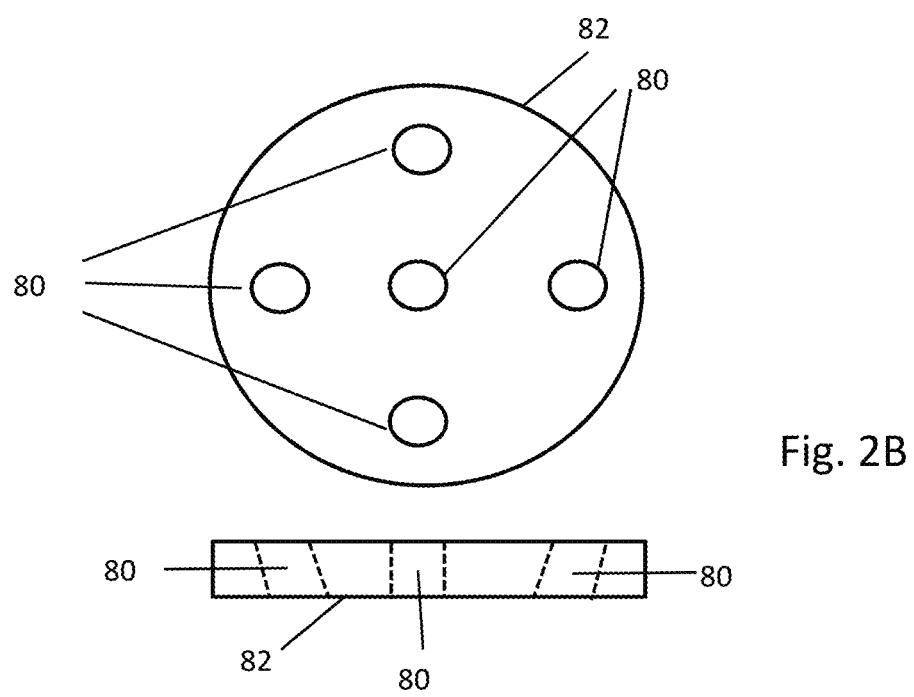

The tool assembly 30 attached to the robotic arm 27 of the image-guided robotic system 25 may comprise an energy delivery device or tool 40 and a corresponding control module responsible for controlling the energy delivery device 40 to deliver a pre-determined energy value to a treatment location (e.g., a particular area of the body surface) at a selected orientation. Alternatively the control module(s) may be at another location and the necessary interconnections may be provided to enable the control module to operate the energy delivery device accordingly. The tool assembly 30 may comprise power unit 22, for example, within its housing, the power unit generates the energy which is delivered to the energy delivery device or tool 40, which in turns transmits the energy to the targeted treatment locations. In some configurations, the tool assembly 30 may comprise at least two energy delivery devices attached to the robotic arm 27 and corresponding control module(s), as described in more detail in reference to FIGS. 2A and 2B. In one configuration for example, as illustrated in FIG. 2A, the at least two energy delivery devices 70 may be disposed within a housing or module 72, with an indexing mechanism 74 which indexes the housing around a center 76, allowing selection of one of the at least two energy delivery devices 70. In another configuration for example, as illustrated in FIG. 2B, the at least two energy devices 80 may be disposed within a housing or module 82, but configured such that they are all directed, or substantially focus towards a single point. Directing to and focusing towards the single point may utilize additional lenses or other such components as may be appropriate, the components attached to the housing or module 82, or at another location. In this manner, indexing of the housing is not required, and selection of one of the at least two energy devices 80 is achieved by activating or switching the selected energy device to its "on" state. Those energy devices 80 that are not activated or not switched "on" are by default not selected. The housing or module 72, 82 shown by example in FIGS. 2A and 2B may be linear, cylindrical, circular, or take any other form which achieves the objective. Preferably the housing or module 72, 82 may be easily detached from the system 25 and connected back into the overall system, thus allowing for various combinations of energy devices to be disposed on different individual housings or modules 72, 82, for easy selection by the operator.

The robotic arm 27 has a base mounted on a stable platform. A patient with a body surface (on which the procedure is to be performed) is positioned relative to the robotic arm 27, so that a targeted body surface is directly in line with the direction that the energy delivery device 70, 80 will transmit.

Figure 1A:
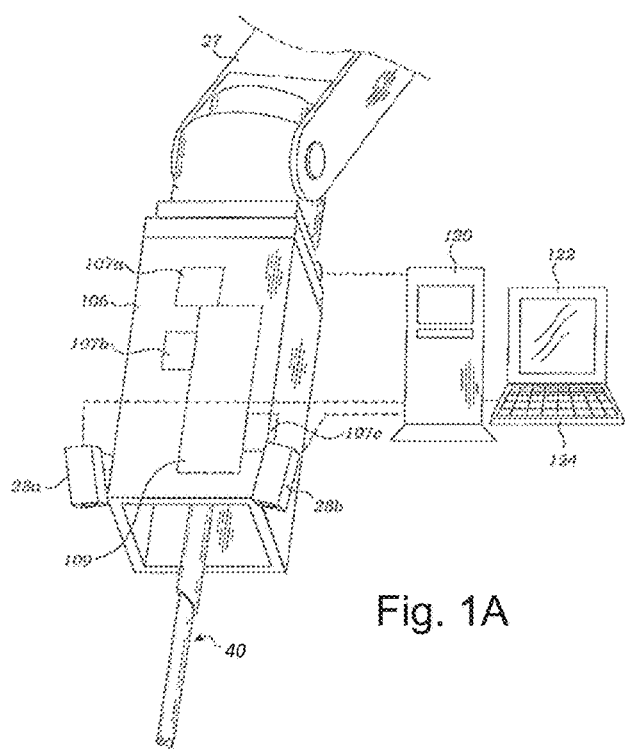
FIG. 1A is an example of a tool having a positioning assembly in accordance with some embodiments.

FIG. 1A illustrates a distal portion of the robotics system 25 in accordance with some embodiments. The robotics system 25 may include a force sensor (not shown) and a positioning assembly 106. The force sensor may be located within the positioning assembly 106 and configured, for example, to sense forces Fx, Fy, Fz in three different orthogonal directions X, Y, Z. As shown in FIG. 1A, the force sensor may be coupled to a computer 120, which receives data from the force sensor. In the illustrated embodiment, the positioning assembly 106 may include a holding unit 109 for engagement with the tool 40, and may also have a plurality of positioners 107a-107c (if applicable). The holding unit 109 is configured to engage with different parts of the tool assembly 30 so that the tool assembly as a whole may be positioned by the positioning assembly 106. In some embodiments, the positioning assembly 106 may include one or more motors for moving different components of the tool assembly 30. For example, in reference to the systems for use in hair removal or delivery of energy to the targeted object (such as hair), the positioning assembly 106 may have components to provide positioning and aiming functionality for the energy delivery tool. For example, the energy delivery device may comprise a targeting assembly for directing the energy transmitted by the energy delivery device in a desired direction at the control of the processor or the controller. Those skilled in the art will be aware that, for example, the targeting assembly may comprise one or more mirrors, lenses, or other such accessories to control the direction that energy is delivered. In other configurations, the energy delivery device may also be mounted on a separate targeting assembly which is attached to the distal end of the robotic arm 27. The targeting assembly may be configured to provide some limited motion (typically less than the motion provided by the robotic arm 27) and aiming of the energy delivery device.

As described in greater detail herein, movement of the robotic arm 27 is governed by a system controller (not shown), in response to control signals derived from image data acquired, for example, by a pair of "stereo" cameras 28 attached to the distal end of the robotic arm (proximate the end-effecter assembly 30). In alternate embodiments, only a single camera need be used for image acquisition. Also, as depicted in FIG. 2 (and also as described in greater detail herein), multiple pairs of stereo cameras 28A and 28B may be used in order to capture differing (i.e., broader and narrower) fields-of-view. In still further embodiments, a single camera may be used to capture a first (i.e., broad) field-of-view, and a second camera may be used to capture a second (i.e., narrow) field-of-view. Other camera configurations are also possible, the cameras being mounted, for example, at any suitable location on or off the robotic arm 27, for example, on a housing of the tool assembly 30.

Image data acquired by the camera(s) 28 is processed in a computer 120 (shown in FIG. 1A) associated with the robotics system 25, which provides control signals to the system controller for directing movement of the robotic arm 27. In particular, images are acquired from each camera of the pair 28 at a desired magnification (e.g., in a range of 6× to 10× in one embodiment) and duty cycle (e.g., 30 hertz in one embodiment). The acquired images are digitized using known image segmentation techniques implemented in a processor, which is operatively coupled to the cameras 28, or in software on the computer in order to identify the position(s) and orientation(s) of objects of interest. In the case of procedures involving the removal or implantation of hair follicles, it may be desirable to die the hair follicles of interest with a dark color prior to a procedure or acquire the image using a different color of light, in order to increase the effectiveness of the image processing techniques. It may also be desirable to cut or shave (in some instances) the hair follicles in the region(s) of interest to a substantially uniform length prior to the procedure.

As will be appreciated by those skilled in the art, one can visualize below the skin surface by adjusting the lighting, filters on the cameras, and various image processing techniques. This is because the reflection and absorption of light by the skin surface will change based on the wavelength of light used. Further, the depth of penetration of the light itself into the skin also varies based on the wavelength. Understanding these basic properties of light, images of the subcutaneous portions of the follicular units (hair follicles) may be obtained using appropriate respective wavelengths of light, including both visible light spectrum and infrared, capturing the different wavelengths of light using different imaging filters, and subtracting and/or combining images during image processing. This approach enables one to visualize the hair shaft of the follicular unit, both outside the skin, as well as under the skin surface, including all the way down to the bulb. Other optical techniques to see beneath this skin surface may also be utilized.

More particularly, the robotics system 25 is able to precisely track movement of the distal end plate (and end-effecter tool or assembly) in each of the six degrees of freedom (x, y, z, ω, ρ, r) relative to three different reference frames. A "world frame" has its x,y,z coordinate origin at a center point of the base 32 of the robotic arm 27, with the x-y coordinates extending along a plane in a surface of a table 36 on which the base 32 of the robotic arm 27 is attached. The z-axis of the world frame extends orthogonally to the table surface through a first section of the robotic arm 27. A "tool frame" has its x,y,z coordinate origin established at the distal end tool plate. Lastly, a "base frame" may be registered relative to the world and tool frames. Each camera also has a (two-dimensional) camera coordinate system ("camera frame"), in which the optical axis of the camera ("camera axis") passes through the origin of the x,y coordinates. By aligning the respective world frame, tool frame, base frame and camera frames, the system controller can precisely position and orient an object secured to the tool plate (e.g., a needle) relative to another object, such as a hair follicle extending out of a patient's skin surface.

Figure 4:
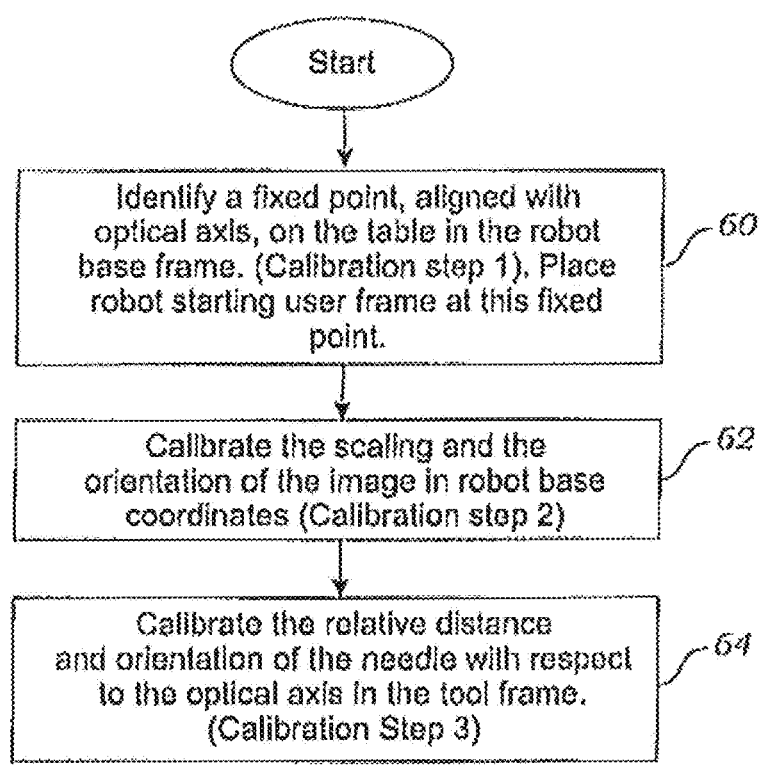
FIG. 4 is a flow diagram of a procedure for calibrating an optical axis and associated camera reference frame of a single camera with a tool frame established at the distal (working) end of the robotic arm to which the camera is attached.

In order to physically align the camera axis with an axis of an end-effecter tool (e.g., an elongate needle cannula) fixed to the distal tool plate of the robotic arm 25, it is of practical importance to be able to calibrate, and thereby have the information to compensate for, the positional and rotational offsets between the end effecter "tool axis" and the camera axis, as well as the deviation from parallel of these respective axes. An exemplary calibration procedure is illustrated in FIG. 4. As an initial matter, the proximal base of the robotic arm 27 is mounted to the table surface 36, so that the table surface 36 is aligned with the x-y coordinate plane of the world frame of the robotic system. Thus, a point lying anywhere on the table surface has a x-y coordinate location in the world frame, which can be identified in terms of x and y offset values (e.g., measured in mm) from the origin of the world frame located at a center point of the robotic arm proximal base interface with the table surface 36, with the z coordinate location of the point in the world frame equal to zero.

At step 60, the camera axis of a single camera fixed to the distal end tool plate of the robot arm 27 is aligned with a fixed "calibration point" located on the table surface 36. The base frame of the robotic system is then initiated, meaning that the origin of the base frame is set at the "calibration point" and the camera axis is aligned with the calibration point on the table surface. This initial position is called "home" position and orientation, and the robot arm 27 always starts from this position, even in the absence of the calibration point.

At step 62, a scaling and orientation of the camera image relative to the base frame is then determined by first moving the robotic arm 27 (and, thus, the camera) a fixed distance (e.g., 5 mm) along the x axis of the base frame, so that the calibration point is still captured in the resulting image, but is no longer aligned with the camera axis. Because the camera frame x-y axes are not aligned with the base frame x-y axes, movement along the x axis of the base frame results in movement in both the x and y directions in the camera frame, and the new location of the calibration point is measured in the camera frame as a number of image pixels in each of the x and y directions between the pixel containing the relocated camera axis and the pixel containing the calibration point.

This process is repeated by moving the robotic arm 27 (and camera) a fixed distance (e.g., 5 mm) along the y axis of the base frame, and again measuring the x,y offsets in the camera frame of the new location of the calibration point. As will be appreciated by those skilled in the art, these measurements allow for scaling the physical movement of the robot/camera (in mm) to movement of an object in the camera image (in pixels), as well as the in-plane orientation of the x-y axes of the camera frame relative to the x-y axes of the base frame. It will further be appreciated that the scaling and orientation process of steps 60 and 62 are repeated for each camera in a multiple camera system, whereby variances in image movement between respective cameras may also be determined and calibrated.

At step 64, once the camera frame is calibrated with respect to the base frame, the camera axis is again aligned with a fixed calibration point lying on the surface of table 36, wherein the base frame is returned to is "home" position and orientation (0,0,0,0,0,0). The robotic arm 27 is then moved in one or more of the six degrees of freedom (x, y, z, ω, ρ, r), so that an end effecter tool (e.g., needle tip) attached to the tool plate contacts the calibration point. By precisely tracking the movement of the robotic arm 27 from the initial home position/orientation of the tool frame to its position/orientation when the tool tip is contacting the calibration point, the system controller calculates the translational and rotational offsets between the initial home position and the camera axis. Because the camera is fixed to the tool plate, the measured offsets will be constant, and are used throughout the procedure for alignment of the tool frame with the camera frame (and, by extension, the base frame).

As will be described in greater detail herein, when using a stereo pair of cameras, e.g., camera pair 28 in FIG. 1, the respective optical axes (and camera frames) of the cameras are typically not installed or maintained in parallel, but are slightly verged, e.g., about 10 degrees, which may be compensated for through known image processing techniques. In particular, the respective camera frames are aligned to have a common x (horizontal) axis, whereby a position and orientation (including in-plane depth) of objects captured in the parallel images may be aligned using image-processing techniques. One advantage of using a stereo camera pair 28 is that a "depth" in the camera frame of an identified object may be calculated based on the differences of the x,y position offsets of the object in the respective (left v. right) camera frames.

In order to calculate a depth of a selected object, such as a hair follicular unit, the left and right images obtained from the stereo camera pair must first be aligned. Because the respective camera images are aligned horizontally, the same objects will appear in the same horizontal scan lines of the two images. And, because the depth of an object being imaged relative to the camera lenses is within a known range (e.g., established by the focal lengths of the respective cameras), a selected object in a first image (e.g., a hair follicular unit) can be matched to itself in the second image (to thereby align the images with each other) by calculating an effective depth of the object when paired with the possible candidate objects in the second image (i.e., in the same scan line) to determine which "pair" has a calculated depth in the possible range.

Another advantage of using a stereo camera pair 28 is the ability to obtain image data regarding the position and orientation of an end-effecter tool (e.g., a hair follicular unit harvesting tool 40 shown in FIGS. 2 and 3, or an energy delivery device such as a laser) in a same reference frame that image data is obtained regarding the position and orientation of objects of interest (e.g., hair follicles, wrinkle lines, tattoos, moles, etc.) on the skin surface. The respective left and right camera frames are calibrated with the tool frame in the same manner as described above for a single camera frame. Once these offsets are established, the relative positions and orientations of the end-effecter tool and objects on the skin surface (e.g., hair follicular units) may be determined and tracked in the tool frame.

Figure 5:
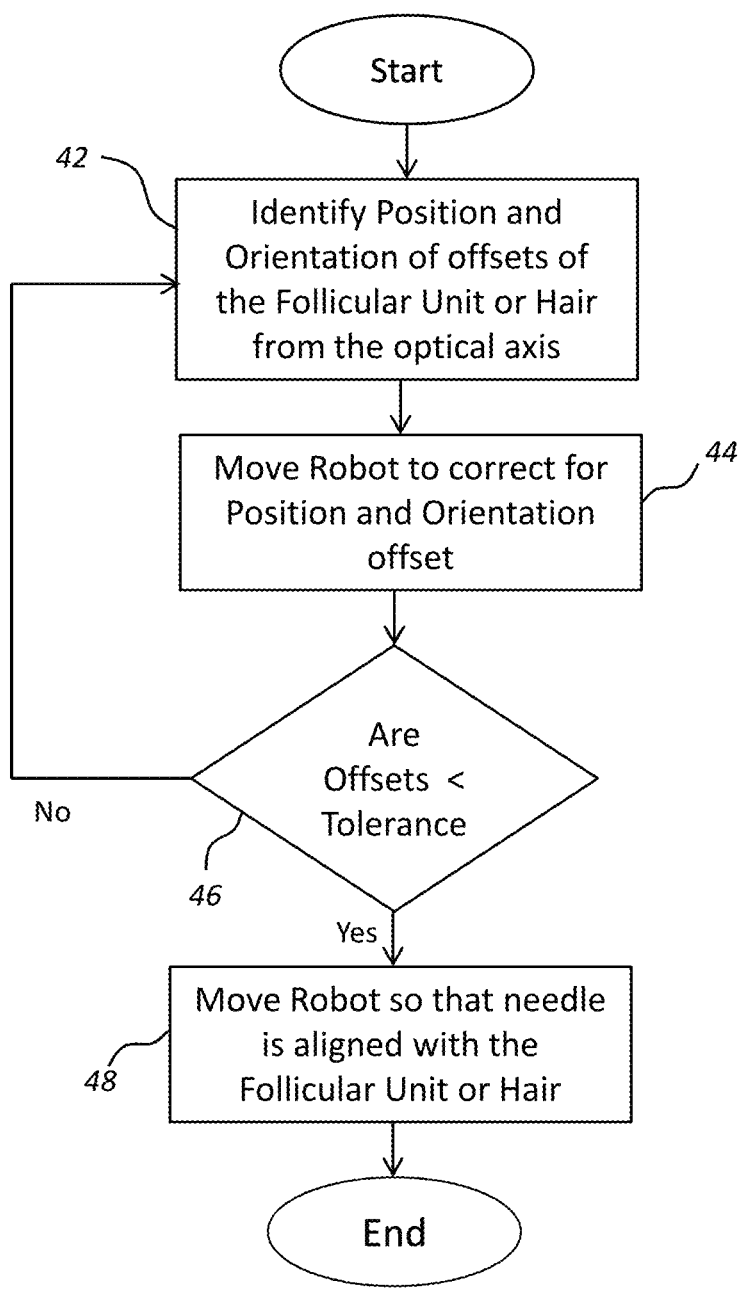
FIG. 5 is a flow diagram of an iterative procedure for aligning (both position and orientation) an elongate end-effecter tool, for example, a tool used for harvesting and/or implanting hair follicles with a selected hair.

FIG. 5 is a simplified flow diagram of a procedure according to one embodiment of the invention for aligning the position and orientation of an elongate axis of the follicular unit harvesting tool 40 with an elongate shaft axis of a hair follicular unit extending from the scalp, using only a single camera for image acquisition. Briefly, the harvesting tool 40 generally comprises a hollow, tubular cannula having a sharpened distal end for puncturing the epidermis and dermis immediately around an outer circumference of a follicular unit in order to envelop, capture and remove the entire follicular unit from the fatty subcutaneous tissues underlying the dermis, e.g., by rotating the cannula in a drill-like motion, or by a quick reciprocating thrust along its longitudinal axis. The harvesting tool 40 may be advanced and withdrawn by its own longitudinal motion (i.e., relative to the tool plate to which it is attached), or by longitudinal motion of the robotic arm 27, or by a combination of both, in order to core and remove the respective follicular units, e.g., by friction and/or with the aid of a weak vacuum. For example, the end-effecter may have its own controller and actuation system that is separate from the robotics system 25.

It should also be appreciated that the positioning and orientation process used for aligning the elongate axis of the harvesting tool 40 with the elongate axis of a hair follicular unit will have much broader applicability than just for hair removal and/or implantation procedures. By way of non-limiting examples, substantially similar positioning and orientation procedures may be used for aligning a laser, or an injection needle, with desired physical features and/or locations on a patient's skin surface in a timely and precise manner.

Figure 7:
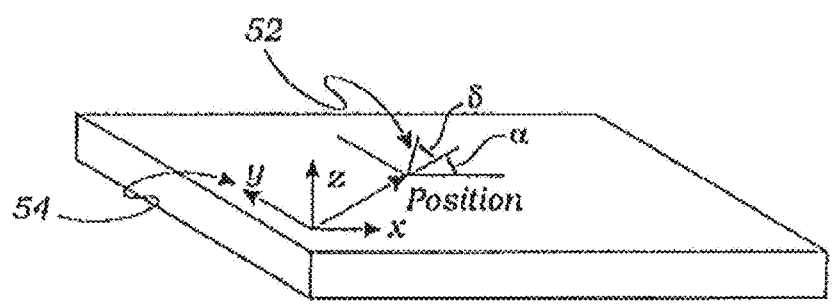
FIG. 7 illustrates exemplary position and orientation, i.e. defined by x,y offsets and in-plane and out-of-plane angles, of a hair relative to the camera reference frame.
Figure 6:
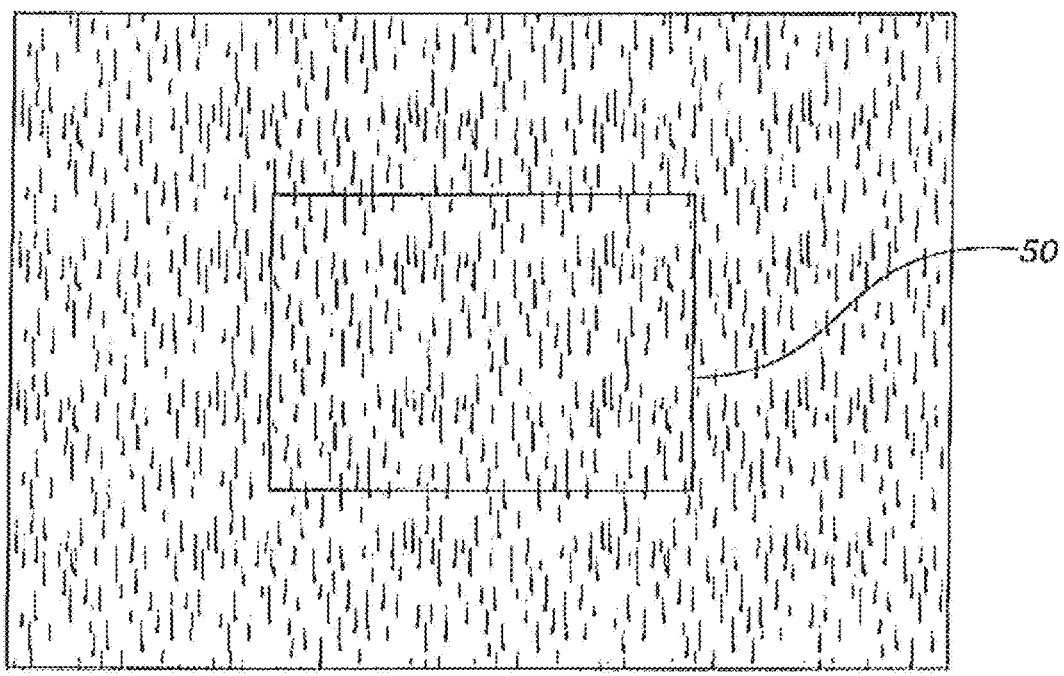
FIG. 6 depicts a camera image of hair follicular units in a region of interest on a human scalp.

After the robotics system 25 has been initiated and calibrated so that the camera frame is aligned with the tool frame (described above in conjunction with FIG. 4), image data is acquired and processed by the system computer to identify objects of interest in the camera frame. By way of example, FIG. 6 depicts, a camera image of hair follicular units in a region of interest 50 on a human scalp. From images of this region of interest 50, image segmentation and screening software residing in the computer identifies and selects one or more particular hair or follicular units of interest for removing from the scalp. With reference to FIG. 7, a position of a selected hair or follicular unit 52 is identified in terms of its x,y offset coordinates in the camera frame (the z axis being the camera optical axis which is preferably aligned substantially orthogonal to the surface of the scalp at the region 50).

Unless the camera axis happens to be exactly aligned with the longitudinal axis of the follicular unit 52 (in which case the follicular unit will appear as a circular point representing an end view of the hair shaft), the image of follicular unit will be in the form of an elongate line having an "apparent" length that will depend on the angle of the camera frame relative to the follicular unit. Because of physical attributes of a hair follicular unit, its base (i.e., the end emerging from the dermis) can be readily distinguished from its tip as part of the image segmentation process. For example, the base portion has a different profile and is generally thicker than the distal tip portion. Also, a shadow of the follicular unit can typically be identified which, by definition, is "attached" at the base.

The x,y locations of the follicular unit base in the camera frame are then calculated and represent the position offsets of the hair base. Orientation offsets of the follicular unit 52 are also calculated in terms of (i) an in-plane angle α formed by the identified follicular unit shaft relative to, and in the same plane as, the x (or y) axis of the camera frame; and (ii) an out-of-plane angle δ that is an "apparent" angle formed between the follicular unit shaft and the scalp, i.e., between the follicular unit and the plane of the x,y axes of the camera frame. As noted above, the hair shaft is preferably trimmed prior to the procedure to a substantially known length, e.g., 2 mm, so the out-of-plane angle δ may be calculated based on a ratio of a measured apparent length of the image of the follicular unit to its presumed actual length, which ratio is equal to the cosine of the out-of-plane angle δ.

Returning to FIG. 5, at step 42, the x,y position and orientation offsets are identified for a selected hair follicular unit or hair follicle, as described above. The computer then calculates the necessary movements of the robotic arm 27 to cause the camera axis to be aligned in the same position and orientation of the calculated offsets. The base frame and tool frame are also "moved" by the same x,y and rotational offsets (i.e., until angles α and δ are both equal to 0), so that the camera, base and tool frames remain aligned at the new position and orientation of the camera axis. Because of the inherent possible variances and errors in the system and in the assumptions (e.g., regarding the hair follicular unit length) the actual position and orientation of the hair follicular unit may not match the calculated values. Thus, once the robotic arm 27 (and camera axis) is moved by the calculated positional and rotational offsets, the follicular unit is again imaged and (at step 46) a determination is made as to whether the camera axis is aligned with the position and orientation of the follicular unit within acceptable tolerances. If the camera axis is adequately aligned with the follicular unit, the robotic arm 27 is moved a last time (at step 48) in order to align the harvesting tool 40 in the "confirmed" position of the camera axis (i.e., based on the offsets obtained in the above-described calibration process). However, if the (in step 46) the camera axis is not adequately aligned with the hair follicular unit, the procedures in steps 42-46 are repeated, starting from the new camera axis location.

As will be appreciated by those skilled in the art, in embodiments of the invention, the duty cycle of the image acquisition and processing is substantially faster than the movement of the robotic arm 27, and the process of identifying and calculating position and orientation offsets of selected hair follicular units relative to the camera axis can effectively be done "on-the-fly," as the robotic arm is moving. Thus, the end destination (i.e., position and orientation) of the robotic arm 27 (and harvesting tool 40) may (optionally) be constantly adjusted (i.e., fine tuned) as the harvesting tool 40 is moved into alignment with the follicular unit. Because such adjustments begin immediately, movement of the robotic arm 27 is more fluid and less jerky. This iterative feedback process, referred to as "visual-servoing," continually calculates and refines the desired position and orientation of the harvesting tool 40.

In some embodiments, the positioning and orientation process, as described herein, may be used to align the elongate axis of the tool 40 with the elongate axis of the visible portion of the hair shaft above the skin surface. In other embodiments, however, it may be desirable to align the elongate axis of the tool 40 with an elongate axis of the portion of the hair shaft under the skin, as described below in reference to FIGS. 5A-5B. Hair follicles do not maintain the same direction of growth under the skin. Quite often a hair follicle significantly changes its direction or angle underneath the skin, such that the orientation of the portion of hair shaft above the skin differs from the orientation of the portion of the hair shaft below the skin. Generally, it has been observed that an emergence angle of the hair from the skin is more acute than its subcutaneous course. As a result, it was discovered that aligning the tool, for example, a laser or other hair removal tool, with the subcutaneous axis of the hair (according to its anticipated position) instead of the visible axis above the skin may result in better targeting and more effective transfer of energy to the portion of the hair that includes critical structures of the follicle containing follicular stem cells and melanocytes responsible for hair growth. These structures/parts of hair (e.g., hair bulb, sebaceous glands, outer root sheath) are typically all positioned along the subcutaneous portion of the hair shaft. Furthermore, such aligning may also reduce the energy that is transferred to the skin itself, and therefore, reduce pain and/or negative effects on the skin.

Figure 5A:
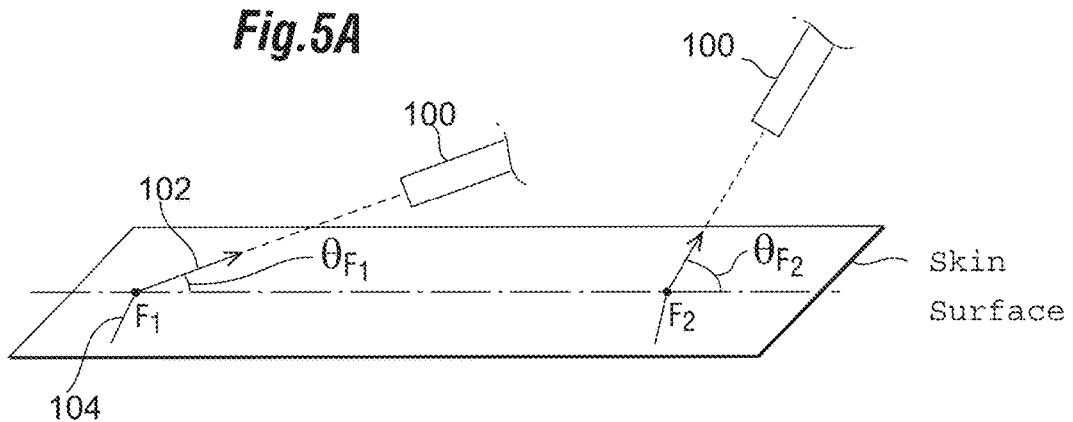
FIGS. 5A and 5B demonstrate examples of some alternative alignment/orientation of the energy delivery device relative to the hairs according to the present disclosure.

As seen in FIG. 5A, the hair or follicle identified as $F_1$ has "above the skin" shaft portion 102, "below the skin" shaft portion 104 and an emergence angle $\theta_{F1}$. As could be seen from FIG. 5A, the emergence angle $\theta_{F1}$ of follicle $F_1$ is fairly acute, and there is a substantial difference between the directions of the hair shaft portions 102 and 104, the below the skin shaft portion 104 having less acute subcutaneous direction. The hair follicle $F_2$, on the other hand, has more upright emergence angle and the above the skin portion of the hair shaft of hair follicle $F_2$ and subcutaneous portions of the hair shaft of hair follicle $F_2$ are closer to parallel. Therefore, if aligned with the above the skin portion 102, the chances of the beam from the energy delivery device 100 missing a targeted for destruction subcutaneous portion of the hair and instead intersecting with skin tissue is comparatively higher than that of hair $F_2$. It is because the hair $F_1$ is shown lying almost flat on the skin surface. When aligned to the visible portion of $F_1$, the tool 100, such as an energy delivery device (e.g., laser), will have a greater tendency to potentially cause unnecessary pain to the patient, without the benefit of depilation or removal of the hair $F_1$. In contrast, if the tool 100 substantially aligns to the visible portion of hair $F_2$, since the orientation of the hair shaft beneath the skin is close to the orientation of the hair shaft above the skin, there will be a greater potential of successful depilation or removal of the hair $F_2$ and less collateral damage to the surrounding skin.

Figure 5B:
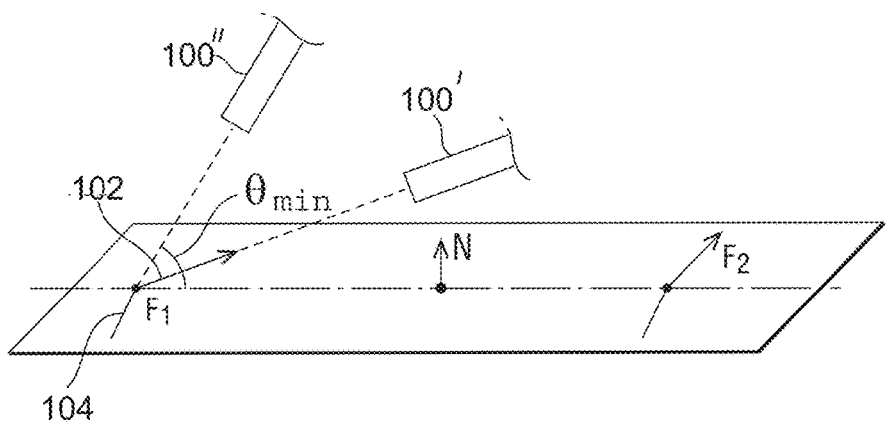

According to a further aspect of the present disclosure, FIG. 5B illustrates a method of orienting the tool relative to the hair follicle of interest according to certain embodiments. Based on various factors and certain characteristics, including the parameters of the energy delivery device utilized, such as spot size, or depth of penetration due to wavelength, for example, it has been determined that there exists a cut-off tool approach angle $\theta_{min}$ (also referred to as "minimum approach angle" of a tool) below which the tool shall not be aligned with the hair to be removed. It is so because, for example, the chance of the beam from the energy delivery device 100 being directed to the skin tissue rather than the hair shaft (including various targeted for destruction components responsible for hair growth) is comparatively higher. In other words, if the emergence angle of the follicle $\theta_F$ is less than the minimum approach angle $\theta_{min}$, then instead of aligning the axis of the tool with the visible portion of the shaft of the follicular unit, the user shall align the tool with such minimum approach angle $\theta_{min}$, which would more closely correspond to the angle of the subcutaneous portion of the hair shaft. It is suggested that the cut-off or minimum tool approach angle $\theta_{min}$ must be selected in the range of, approximately, 40° to 65° and preferably, in the range of 45° to 55°, and even more preferably, in the range of 50° to 55° for certain tools and applications. It will be appreciated that although the embodiment above has been described with respect to a minimum approach angle, a maximum approach angle can also be determine and used in some embodiments. This maximum approach angle can be used, for example, to dictate the tool angle that should be utilized for those follicles that emerge at an angle above the maximum approach angle. For example, a maximum tool approach angle $\theta_{max}$ may be defined in a range of 45 to 90 degrees. FIG. 5B demonstrates that since the emergence angle of the above the skin hair shaft portion 102 of follicle $F_1$, is less than the minimum approach angle ($\theta_{F1} < \theta_{min}$), the system does not align the axis of the tool to the portion 102 (as would be indicated by the representation 100'), but instead aligns/orients the axis of energy delivery tool to the minimum approach angle $\theta_{min}$ as indicated by 100'' (which is substantially parallel or at least closer aligned to the under the skin portion 104 of the hair shaft of follicle $F_1$.)

In some embodiments, in order to increase the throughput of a system, an emergence angle of a hair of interest may be determined as a group representative emergence angle based on the information from a plurality or a group of hair follicles of interest. For example, an image of the group/plurality of follicles is first obtained. The emergence angle of each hair follicle in the group, or a representative number of, or a predetermined number of the group of hair follicles may be determined, and an average or mean value of the determined emergence angle calculated. For example, it may be beneficial to average an emergence angle of hair follicles in a selected neighborhood (e.g., 100 hair follicles; or visible hair on a screen of a user display, or within 25 mm radius of a selected hair follicle, etc.). Averaging eliminates individual noise, and with reference to the robotic systems it increases the speed and efficiency of the procedure because it requires less reorientation and movement of the tool. A minimal approach angle of a tool may be chosen, for example, based on any one or combination of the following: a particular application or treatment involved, statistical information about the patient, the area of the body surface, physical limitations related to the tool and/or the patient, just to name a few factors. Then the average or mean value of the determined emergence angle of the group of hair follicles (which is now used to represent an emergence angle of a hair follicle of interest) is compared with the minimum approach angle of the tool. Based on a result of the above comparison, the tool is oriented relative to each of the hair follicles of the group at the same approach angle. In this manner the number of re-orientations that the tool has to undergo during a treatment session can be minimized, and efficiency increased. As stated before, if the determined "group representative" emergence angle of the hair follicle of interest is less than the selected minimum approach angle, the tool is oriented to the minimum approach angle.

According to another embodiment, the following logic for the angle adjustment and tool orientation may be implemented. The minimum approach angle is compared to the emergence angle of the hair follicle of interest and the following logic may be applied based on the results of such comparison:

a) If the minimum approach angle is higher than the emergence angle of the hair follicle of interest, then the minimum approach angle may be used as the actual tool approach angle for that particular hair follicle. However, as an example, the following modification may be superimposed on this initial logic. For example, if the difference between the minimum approach angle and the emergence angle of the hair follicle of interest is less than a selected number of degrees (e.g., 5° or 10°), it may be desirable to choose a tool approach angle which is substantially equal to the sum of the selected number of degrees and the emergence angle of the hair follicle of interest.

b) If the minimum approach angle is the same or lower than the emergence angle of the hair follicle of interest, then the emergence angle of the hair follicle of interest may be used as the tool approach angle. However, again the following modification may be super-imposed on this initial logic. For example, it may be desirable to choose the tool approach angle, which is substantially equal to the sum of the selected number of degrees and the emergence angle of the hair follicle of interest. In some instances, if the emergence angle of the hair follicle of interest is greater than the minimum approach angle by more than a predetermined value, the tool may be oriented to an angle that is above the minimum approach angle but not more than a sum of the minimum approach angle and the predetermined value (e.g., an angle equal to a sum of the minimum approach angle and the predetermined value).

According to yet another embodiment, an alternative method for the angle adjustment and tool orientation may be implemented. In some embodiments, the method of orienting a tool may comprise determining an emergence angle of a hair follicle of interest, choosing a predetermined offset angle, and orienting the tool relative to the hair follicle of interest based on the determined emergence angle of the hair follicle of interest and the predetermined offset angle. With reference to procedure for hair removal or depilation, the predetermined offset angle may comprise an angle of anywhere from 0 to 45 degrees, for example, between 10-20 degrees. The predetermined offset angle may be based on pre-existing data of the recipient, pre-existing data from other recipients, or data collected via other reputable sources, otherwise referred to as historic or statistical data. For purposes of procedures other than hair removal, the predetermined offset angle may be determined as appropriate for each relevant procedure and body surface, and it may range between 0 and 90 degrees.

According to further aspect of the present disclosure, the image-guided robotics system similar to those shown by example as system 25 may be used to perform automated or semi-automated procedures for identifying position and orientation of a large number of hair follicles or follicular units in a region of interest, and then accurately harvest or remove some or all of the follicles or follicular units. One or more cameras attached to the working distal end of the robotic arm capture images at a desired magnification of a selected area of the patient's scalp or other body surface. A computer system processes the images and identifies (through known thresholding and segmentation techniques) the individual hair, as well as their respective positions and orientations relative to the camera frame. With reference to hair transplantation, through a user-interface (e.g., a display and a standard computer mouse), an attending surgeon may define a region on the scalp from which hair follicular units are to be harvested and defines a harvesting pattern, such as, e.g., taking every other hair follicular unit in the region, leaving a defined number of follicular units between harvested follicular units, taking a certain percentage of follicular units, leaving behind an aesthetically acceptable pattern, etc.

For example, images obtained from a wide field-of-view pair of stereo cameras may be used by the attending physician to locate generally a region of interest, while images obtained from a narrow field-of-view pair of stereo cameras are used to accurately guide the harvesting tool with the individual selected follicular units. Once the hair follicular units to be harvested have been identified, the robotics system systematically aligns a harvesting tool (e.g., harvesting tool 40) with each hair to be harvested; the respective hair follicles are harvested, and the process is repeated for all of the selected follicular units in the defined harvest region. It will be appreciated that in some cases, the individual hair follicular units being harvested are then implanted in another portion of the patient's scalp, whereas in other instances the harvested hair follicular units are discarded. It will also be appreciated that, rather than a coring harvesting tool, such as tool 40, another type of hair removal end-effecter tool may be employed, such as, e.g., a laser. It will be still further appreciated that the above-described techniques for aligning the camera frame with the robot tool frame for precisely aligning an end-effecter tool may be equally applicable to other types of end-effecter tools, such as energy delivery devices, laser, a fiber optic cable for delivering a beam, an injection needle (or a plurality of injection needles) used for injecting ink for forming tattoos on a skin surface of a patient.

Figure 8:
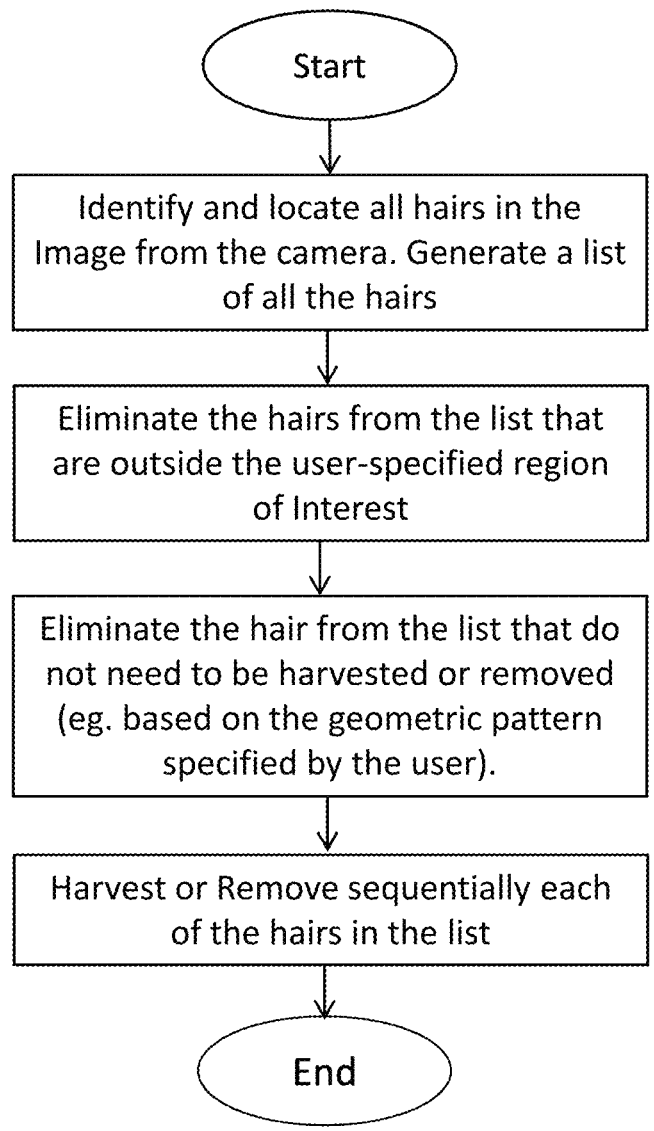
FIG. 8 is a flow diagram of an automated procedure for identifying a position and orientation of each of a multiplicity of hair follicles in a region of interest, for example, on a human scalp, and then removing some or all of the identified hair follicles or follicular units.

FIG. 8 is a flow diagram of an automated (or semi-automated) procedure for identifying a position and orientation of all follicular units or hair in a region of interest, and then accurately harvesting or affecting removal of some or all of the identified follicular units or hair follicles.

Figure 9:
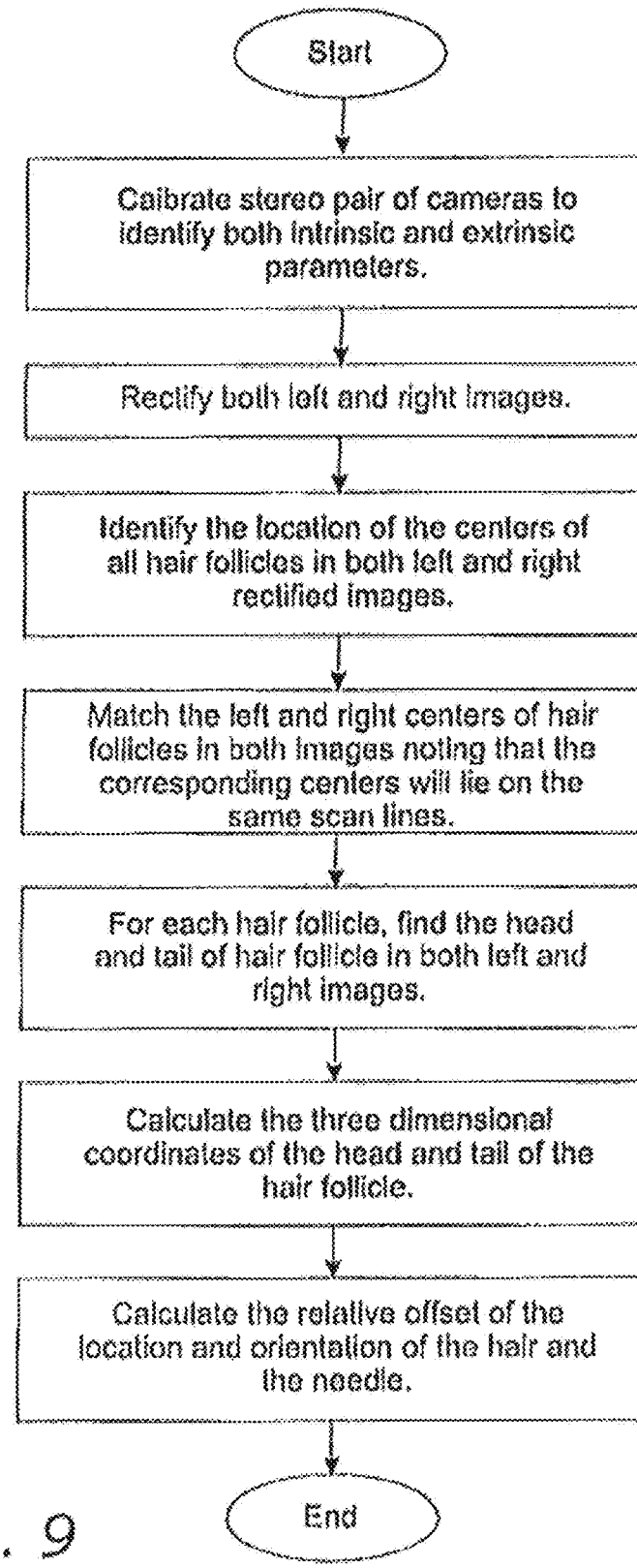
FIG. 9 is a flow diagram of an algorithm that uses images acquired from a stereo pair of cameras for identifying follicular units or hair in a region of interest, and then computes the respective locations and orientations of the identified follicular units or hairs.

FIG. 9 is a flow diagram of a procedure using a stereo pair of cameras to identify individual follicular units in a region of interest, and then compute a location and orientation of each in the respective camera frames and robot tool frame. The procedure starts by calibrating the stereo pair of cameras to identify both intrinsic and extrinsic parameters, in accordance with well known techniques. Intrinsic parameters are intrinsic to the individual camera, such as internal optics, distortion, scaling, and the like. Extrinsic parameters relate to characteristics between the two cameras, e.g., differences in the alignment of their respective optical axes (which are ideally parallel to one another, but as since this is unlikely as a practical matter, mathematical compensation is required). Calibration of intrinsic and extrinsic parameters is known in the field of stereo imaging and will not be explained in detail herein. As discussed above, the locations of the centers of the hair follicles are identified and matched in both the left and right rectified images. The head and tail of each hair follicle is then identified in both the left and right images, wherein the three dimensional coordinates of the head and tail of the hair follicle may be calculated. Finally, the relative offset of the location and orientation of the hair follicle and the cannula are determined by employing the images of the cameras which see both the cannula and the hair follicle, in accordance with well known stereo imaging techniques.

It will be appreciated that there are other methodologies known to those in the art that may be utilized to identify individual follicular units in a region of interest, and then compute a location and orientation of each in the respective camera frames and robot tool frame. Some of these methods requiring only a single camera, rather than a stereo pair of cameras. For example, in one embodiment a single camera may be utilized to capture data enabling the individual follicular units to be identified, and a depth sensor (e.g. time-of-flight camera, laser range scanner, structured light scanner) or similar device utilized to capture spatial data, such as distance.

Figure 10:
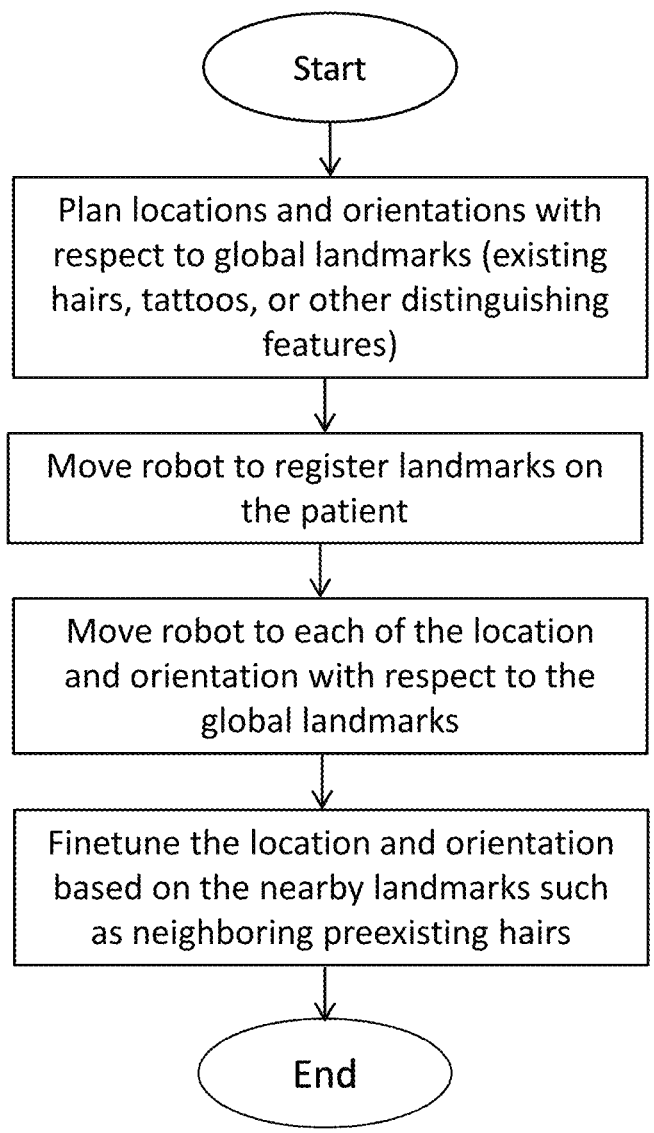
FIG. 10 is a flow diagram illustrating an automatic guidance feature of an image-guided robotics system.

FIG. 10 shows an example of the automatic guidance feature of the robotic system with respect to global landmarks (e.g., existing hairs, tattoos, or other distinguishing features). It will be apparent that this methodology may equally apply to planning various locations, including locations from which hair is to be removed. The robot may be moved to register landmarks on the patient and the registered information may be stored in memory for reference. The robot can make use of the registered landmarks as reference points for recognizing its position relative to the working surface. The robot may be moved to each of the hair removal locations and orientations with respect to the global landmarks. The global landmarks provide a global reference for global movements. The locations and orientations are fine-tuned based on the nearby landmarks such as neighboring preexisting hairs or locations from which hairs have already been removed. The nearby landmarks provide a local reference for local movements.

In accordance with yet another aspect of the inventions disclosed herein, the above-described image processing techniques and embodiments may be employed for diagnostic procedures with or without the robotic system. For example, the robotic arm 27 may be used to maneuver one or more cameras 28 fixed to the distal tool plate, but without any further end-effecter assembly. In the alternative, the one or more cameras may be mounted to a non robotic assembly, whether positionable or rigid, and whether stationary or movable. Or the one or more cameras may be hand held. By way of non-limiting examples, such procedures may include: (i) examination of a patient's skin surface, or below the skin surface; (ii) detection and/or monitoring and/or tracking changes in skin conditions over time; and (iii) for image data acquisition for supporting medical therapies such as the use of lasers, drug delivery devices, etc. Image data acquired by the imaging system can be stored as part of a patient's medical history. Also, image data acquired by the imaging system can be stored, later processed, and/or enhanced for use in a telemedicine system.

According to another aspect, automated systems and apparatus constructed and operated according to various embodiments of the present disclosure may be used, as already stated above, for the controlled application of energy into or through targeted tissue regions for therapeutic and cosmetic hair and skin treatment procedures on a mammalian body. It will be appreciated that the energy being applied may be selected for cosmetic reasons (whether aesthetic, reconstructive, or both), for therapeutic reasons (whether curative or palliative), or for a combination of cosmetic and therapeutic reasons. Various types of energy and numerous different treatments are particularly well suited for application using an automated system according to the present disclosure. As non-limiting examples, all of the types of energy and the energy delivery devices, and all of the hair and skin therapies described above, are compatible with the systems and methods of the present disclosure.

For hair removal, there are three ways light can potentially destroy hair follicles: thermal (due to local heating), mechanical (due to shockwaves or violent cavitation), and photochemical (due to generation of toxic mediators like singlet oxygen or free radicals). Follicular stem cells responsible for hair growth are located in the outer root sheath in an area called the bulge, near the attachment of the arrector pili muscle, approximately 1.5 mm below the epidermis. Thus both bulge and bulb are important targets for permanent hair follicle destruction.

Photothermal destruction of hair follicles is based on the principle of selective photothermolysis. This principle predicts that selective thermal damage of a pigmented target structure will result when sufficient fluence at a wavelength, preferentially absorbed by the target, is delivered during a time equal to or less than the thermal relaxation time ("TRT") of the target. As for suitable light sources, the normal mode 694 nm ruby, normal mode 755 nm alexandrite, 800 nm pulsed diode lasers, long pulsed 1064 nm Nd:YAG lasers, and intense pulsed light ("IPL") technology all employ this mechanism.

In the visible to near infrared region, melanin is the natural chromophore for targeting hair follicles. Laser or light sources that operate in the red or near-infrared wavelength region lie in an optical window of the spectrum, where selective absorption by melanin is combined with deep penetration into the dermis. Deep, selective heating of the hair shaft, hair follicle epithelium and the heavily pigmented matrix is therefore possible in the 600-1000 nm region. However, melanin in the epidermis presents a competing site for absorption. Selective cooling of the epidermis has been shown to minimize epidermal injury. Cooling can be achieved by various means, including a cooled gel layer, a cooled glass chamber or cooled sapphire window, and a pulsed cryogen spray. According to a novel feature of the present disclosure, in some embodiments, cooling is achieved through the use of an automatically controlled air jet, as described in more detail below.

Laser pulse width also appears to play an important role, as suggested by thermal transfer theory. Thermal conduction during the laser pulse heats a region around each microscopic site of optical energy absorption. To obtain spatial confinement of thermal damage, the pulse duration should be shorter or equal to the thermal relaxation time of the hair follicle. It is estimated that the thermal relaxation of human terminal hair follicles is about 10-50 milliseconds (ms), depending on size. Devices for hair removal therefore have pulse durations in the millisecond domain region. A number of typical lasers used for hair removal are listed in the table below, along with several key specifications of each laser, such as the light source and wavelength.

| Light Source | Wavelength (nm) |
| --- | --- |
| Long Pulse - Ruby | 694 |
| Long Pulse - Alexandrite | 755 |
| Diode Laser | 800-810 |
| Q-Switched Nd:YAG | 532/1064 |

In tattoo removal, the target for the laser light consists of small particles of tattoo ink, which are found either within macrophages or scattered extra-cellularly throughout the dermis. For treating benign pigmented lesions, the laser primarily targets melanin as its chromophore. However, unlike laser hair removal, in which the large melanin-laden unit of the hair follicle is the target, treatment of benign pigmented lesions rely upon targeting small particles of melanin found within melanocytes, keratinocytes and dermal macrophages. The targets in both tattoos and benign pigmented lesions are quite small in size. As a result, using the concept of thermal relaxation time to minimize collateral thermal injury to the normal surrounding tissue, the pulses of light required for effective treatment, must be very short. Thus Q-switched lasers with pulse durations in the nanosecond or picosecond range are the mainstay of therapy for both benign pigmented lesions and tattoos. Most of these lasers have pre-set, nonvariable pulse durations that cannot be changed by the operator.

Melanin absorbs light in the 500-1200 nm range. At longer wavelengths, absorption is lower and penetration deeper than at the shorter wavelengths. For example, the Q-switched Nd:YAG (1064 nm) laser emits light that penetrates 2-3 mm into the dermis and is therefore suitable for the removal of deeper dermal pigmentation such as found in Nevus of Ota. By passing the beam though a KTP crystal the frequency is doubled and the wavelength halved (532 nm). The shorter wavelength penetrates more shallowly and is therefore more useful for the removal of epidermal pigment, such as in ephelides (also known as freckles), and solar lentigines (age spots). The ruby (694 nm) laser, which penetrates less than 1 mm into skin is also of most use in treating superficial lesions such as in freckles or café au lait macules.

The Q-switched laser is an electro-optical device which is used to produce pulses of only a few nanoseconds. These are designed to be within the estimated TRT of melanosomes (0.5-1 microsecond (μs)), although longer than that of tattoo particles which have a TRT in the low nanosecond domain. Flashlamps can pulse within a millisecond range, which is relatively long in this context. Nanosecond light may fragment and disperse melanin and tattoo ink, thereby altering its optical properties. Most of the lightening occurs due to gradual uptake and removal of the fragmented particles by activated macrophages through the lymphatic system. Some coloration may also be removed by transepidermal elimination.

Black or blue tattoo pigments absorb radiation across a broad range of wavelengths in the visible and near-infrared spectrum. Green inks respond optimally to the Q-switched ruby (e.g., 694 nm) and Q-switched alexandrite (e.g., 755 nm) lasers but often persist. Conversely, red pigments respond best to the green light emitted by the frequency doubled Nd:YAG (e.g., 532 nm). The Nd:YAG laser is effective for blue-black tattoos but is relatively poorly absorbed by green pigments. Still, it has been used successfully to treat tattoos in pigmented skin. Red, brown, white or skin colored inks that contain iron or titanium oxides can be chemically reduced to a permanent slate-grey or black color during laser treatment. Then, the slate-grey or black color may be faded with subsequent treatments.

Several typical lasers used for tattoo and skin coloration removal are listed in the table below, along with several key specifications of each laser.

| Tattoo Color | Laser | Wavelength (nm) |
|---|---|---|
| Dark blue and black tattoos | Q-s Alexandrite (light skin only) OR | 755 |
| | Q-s Nd:YAG (all skin types) | 1064 |
| Green Tattoos | Q-s Ruby (light skin only) | 694 |
| Red Tattoos | Q-s Nd:YAG (light skin only) | 532 |

Cutaneous vascular lesions are one of the most common indications for laser treatment in dermatology. These vascular lesions include congenital and acquired vascular lesions such as telangiectasia, erythema, hemangiomas, port wine stains (capillary vascular malformation). Treatment of these common conditions is efficacious, well-tolerated and can be tailored for all skin types.

The theory of selective photothermolysis is the ability to target a specific chromophore in the skin without damaging surrounding structures through the selection of the proper wavelength, pulse duration, and fluence. Treatment parameters therefore can be optimized, permitting precise treatment of the intended structure while minimizing collateral injury to other tissues. The target chromophore in the treatment of vascular lesions is oxyhemoglobin. The peaks of oxyhemoglobin absorption are at 18 nm, 542 nm, and 577 nm By selecting oxyhemoglobin, the surrounding vessel absorbs sufficient energy and is coagulated. To minimize thermal injury to surrounding structures, the laser pulse duration should be equal to or shorter than the thermal relaxation time of the intended target. The thermal relaxation time is the cooling time of the target and is proportional to the square of the target diameter. For example, a port wine stain contains blood vessels that average 50-100 microns in diameter. The thermal relaxation time is approximately 1-10 ms. Longer pulse durations than the thermal relaxation time can lead to thermal diffusion and resultant damage to other structures.

Some typical lasers and specifications for vascular lesions are listed in the table below:

| System | Wavelength (nm) |
|---|---|
| PDL (Pulsed Dyed Laser) | 585-595 |
| KTP (Potassium Titanyl Phosphate Laser) | 532 |
| IPL (Intense Pulse Light) | 550-1200 |
| Nd:YAG (Neodymium:Yttrium-Aluminum-Garnet Laser | 1064 |
| Alexandrite | 755 |

Photodamage is the cumulative effects of life-long exposure to environmental UV radiation. It is represented by changes in the skin that include fine to deep wrinkles, skin laxity, and leathery, pebbly, or coarse skin texture. When severe photodamage is present, one may see thinning of the skin, dryness and roughness, dyspigmentation, telangiectasias, and easy bruisability. Photodamage is usually most prominent in the periorbital, perioral, nasolabial, and glabellar areas, so these are usually the areas that prospective patients will be most bothered by. There are a number of diverse laser and light systems that have been shown to be effective for nonablative treatment of photoaging skin. These systems include KTP, pulsed dye, Nd:YAG, diode, erbium:glass lasers and intense pulsed light devices. While historically, ablative lasers were the optimal treatment for photodamaged skin, ablative skin resurfacing has become increasingly unpopular with both patients and physicians due to the significant risks of prolonged recovery time, possible permanent hypopigmentation, and/or scarring. As a result, nonablative skin rejuvenation has become the treatment of choice for photorejuvenation. It offers an elegant, effective, noninvasive treatment for problems related to photodamage and aging.

Ultraviolet-induced photodamage accelerates and magnifies the physiologic changes of the normal aging process. Ultraviolet exposure produces a myriad of changes in the skin, including free radical formation, apoptosis, angiogenesis, melanogenesis, DNA mutations, oncogenesis, immunosuppression, matrix metalloproteinase induction and degradation of connective tissue. The histologic manifestations of photodamaged skin include loss of collagen and abnormal clumping of elastic fibers in the superficial dermis. In addition, ultrastructural analysis shows a thin epidermis, flattened rete, increased vasculature, chronic inflammation, elastotic changes including the accumulation of large amounts of elastic material, wide spaces between the collagen bundles, and random deposition of collagen fibers. These histologic and ultrastructural changes are clinically correlated with rhytides, laxity, yellow discoloration and telangiectasias. Nonablative skin rejuvenationing triggers a wound healing response to restore the normal architecture of collagen in the dermis. Associated vascular damage recruits inflammatory mediators that lead to fibroplasias and homogenization of the collagen.

Clinical photodamage is classified into three types as shown in the table below:

| Photodamage Classification | |
|---|---|
| Type I | Lentigines (brown spots), telangiectasias, increased coarseness, symptoms of rosacea (diffuse redness) |
| Type II | Rhytides, laxity, dermatochalasis |
| Type III | Actinic keratoses, nonmelanoma skin cancers |

Generally, photorejuvenation treatments are performed on the sun-exposed areas of the face, neck, upper chest, and hands. Nonablative skin rejuvenation technology can be categorized into four different general modalities: vascular lasers, mid-infrared lasers, intense pulsed light systems, and radiofrequency devices. The term 'nonablative skin rejuvenation' includes noninvasive rejuvenation, skin toning, and wrinkle reduction due to dermal neocollagenesis, and photorejuvenation due to both epidermal improvement and dermal collagen remodeling.

For more severe photodamage and treatment of wrinkles the $CO_2$ lasers are often used. Reports of successful treatment of wrinkles using the $CO_2$ laser first emerged in the 1980s. Presently, $CO_2$ laser resurfacing remains the treatment of choice for facial rhytides (wrinkles), acne scars and improvement of severe photodamage. It can effectively reduce uneven facial pigmentation, actinic dermatoses, lentigines, textural irregularities, and fine to deep lines. In a precisely controlled manner, it can be used to effectively remove the outer damaged skin layers and promote the development of new collagen and epidermis. Due to the tissue tightening effects and the resulting collagen shrinkage after $CO_2$ laser treatment, a firmer and more healthy appearance results. However, as explained above, those lasers are used when less invasive treatments (e.g., IPL) are not sufficient.

Energy delivery devices implementing radiofrequency tissue tightening may be also used as an alternative to nonablative laser technologies. Due to the deep dermal heating created by the radiofrequency device, a cryogen spray is usually delivered before, during, and after delivery of the radiofrequency energy onto the inner surface of the treatment tip membrane. It provides cooling to protect the dermis from overheating and subsequent damage. The cryogen spray also provides cooling of the upper portion of the dermis. This creates a reverse thermal gradient though the dermis and results in volumetric heating and tightening of deep dermal and even subdermal tissues. The depth of this heating is dependent upon the treatment tip geometry and the duration of cooling.

The automated treatment system 25 of the present disclosure may be utilized to perform any of the therapeutic and cosmetic hair and skin treatment procedures described above. System 25 however, needs to be outfitted with the appropriate tools and one or more energy delivery devices for the relevant procedures, as explained above. Also, the processor(s) and/or controller(s) associated with the system must be configured or programmed to execute the methodology and apply the treatment parameters for the particular energy delivery device and a particular type of treatment. Because the process is automated using an image-guided computer-controller system with the robotic arm 27, any number of movements, as well as precise targeting and energy application may be easily and quickly accomplished. By way of example, the system 25 may be able to perform a movement, targeting and energy application cycle at a frequency of at least 60 cycles per second The robotic system 25 preferably includes a user interface operably coupled to the processor and/or the controller 120 (which may be the same processor used elsewhere in the system 25, or a different processor or controller). As seen in FIG. 1A, the user interface may comprise a monitor 122 and one or more input devices, such as a keyboard 124, a mouse, a pointer, and/or a touchscreen. Alternatively, the user interface may comprise a smart device, a mobile phone, a smart phone, or other such device. The user interface allows a system operator to input treatment parameters and/or instructions relating to one or more of a location, orientation, and distance from the targeted tissue for the energy delivery device, or the system may suggest some parameters automatically. Further, as an example, the system operator may be able to graphically select one or more treatment locations via the user interface. The treatment parameters that may be also input or adjusted via user interface may include, for example, type, intensity, and/or duration of treatment of the therapeutic or cosmetic energy to be delivered to the targeted tissue at the treatment location.

According to a further aspect of the present disclosure, a methodology for planning various treatments and procedures and executing such plans using the automated image-guided system of the present disclosure is provided. For example, in some embodiments, the treatment plan is a prescribed plan designed to transplant hair follicles from a first region (harvest region) to a target region (implant region) in reference to the hair transplantation procedures; or to destroy/remove hairs from a body surface in reference to hair removal procedures. In such cases, depending on treatment application, the treatment plan may include one or more parameters, such as an outer boundary from within which the hairs are to be removed, a number of hair follicles to be removed/implanted, location of harvest region, location of implant region, a degree of randomness associated with targeted implant locations, spacing between adjacent targeted implant locations, depth of follicle, depth of implant, patient identification, geometric profile of harvest region, geometric profile of implant region, marker location(s), and density of targeted implant locations.

Some examples of how the treatment plan may be created using the system 25 are described below. As a preliminary step, the robotic arm 27 may be maneuvered to position an imaging device (e.g., one or more cameras 28) proximate the treatment location so that the cameras 28 may take one or images of the treatment area. Such maneuvering may be substantially automatically achieved, for example, by identifying a boundary of the treatment in the one or more images (a leg, an arm etc.), utilizing fiducials to indicate the treatment boundary, or by manual positioning of the cameras relative to the treatment areas. The images of the treatment location taken by the camera(s) may be received and processed by the processor using various image processing techniques. The processor may determine treatment location data and other information pertinent to the procedure, including but not limited to, specific locations of the unwanted hair, type/classification of hair, caliber, width or thickness of hair, length of hair, angle of hair relative to the body surface, color/pigmentation of hair, color/pigmentation of skin surrounding hair of interest. In some embodiments, the processor may also propose or generate a suggested treatment plan based on the processed images and information. In other embodiments, the images and treatment location data may be displayed on the user interface and the system operator/user may input treatment parameters and/or instructions to the system 25. Alternatively, the user may simply reject or modify the treatment plan automatically proposed by the system.

Various techniques may be used to input the treatment plan into the computer 120. In the illustrated embodiments, the treatment plan may be inputted using a user interface that includes, for example as seen in FIG. 1A, a monitor 122 and a keyboard 124, or a touchscreen, mobile device, smart device, tablet or phone. Alternatively, the treatment plan may be inputted using a storage device, such as a diskette, a compact disk or USB drive. In other embodiments, the treatment plan may be downloaded from a remote server/location, such as via a cloud environment. In further embodiments, the treatment plan may be inputted using a combination of the above techniques. For example, some parameters may be inputted into the computer 120 using a diskette, while other parameters may be inputted using the user interface. In some embodiments, one or more parameters of the treatment plan may be determined in real time (e.g., during a treatment session). As stated before, the treatment plan may be generated by a processor of the automated system 25 based on the acquired images.

Once the treatment planning has been programmed into the system 25, since the system already determined and knows a location and an orientation of each hair in the area of interest, for example for purposes of hair depilation, the robotic arm 27 is maneuvered to position the energy delivery device to aim at a particular hair follicle according to the procedure plan. The system 25 then operates the energy delivery device via the controller, to direct the energy into the target tissue at the treatment location, which is in case of hair removal or depilation is at the targeted hair follicle. In many cases, the treatment location may comprise an area requiring multiple applications of energy by the delivery device in order to treat the entire area, for example, for hair removal from a region of the body surface. In such case, the robotic arm 27 is repeatedly maneuvered to re-position and aim the energy delivery device at each of the hair follicles identified in the procedure plan the region until the entire area of the procedure region has been treated.

According to a further aspect, the systems, apparatus and methods of the present disclosure also eliminate or substantially reduce some of the problems that exist with the existing devices for hair removal, including laser hair removal devices. Existing laser removal techniques apply laser beams to an area of a body surface from which it is desired that hair be removed. Hair which lacks melanin will not be affected by the application of the laser, the laser energy will not be absorbed sufficiently by these hairs, and the melanin-lacking hairs will remain substantially intact. However, application of laser energy (and related heat) to the hair lacking melanin not only will result in wasted efforts, but also potentially may cause discomfort, pain and unnecessary damage to the surrounding tissue. In addition, the application of the laser to areas devoid or lacking of hair, may target deposits of melanin which reside in the surrounding tissue, such as the skin, which will also absorb the laser energy, also potentially causing tissue damage (for example, in the form of heat), and thereby potentially causing discomfort, if not pain to the recipient of the treatment. Moreover, it may cause the skin to darken or lighten (for those with darker skin types), with all this discomfort and/or pain happening without any actual benefit of hair removal or depilation.

Furthermore, typically during a laser hair removal appointment, the recipient of the procedure is treated with a laser that has been selected based on their overall standard skin tone or hair color. The hair removal treatment centers do not typically take into consideration within a particular treatment, any variation in hair or skin pigmentation that may exist within a treatment area, or the existence of one or more new tan lines that a recipient of the procedure may have at a time of a particular treatment session, that is, areas adjacent one another which are can be substantially different from each other in pigmentation/color, one area being paler or darker than the other. The methods and systems of the present disclosure provide solution to many of the issues and problems of the existing devices and procedures.

Figure 11:
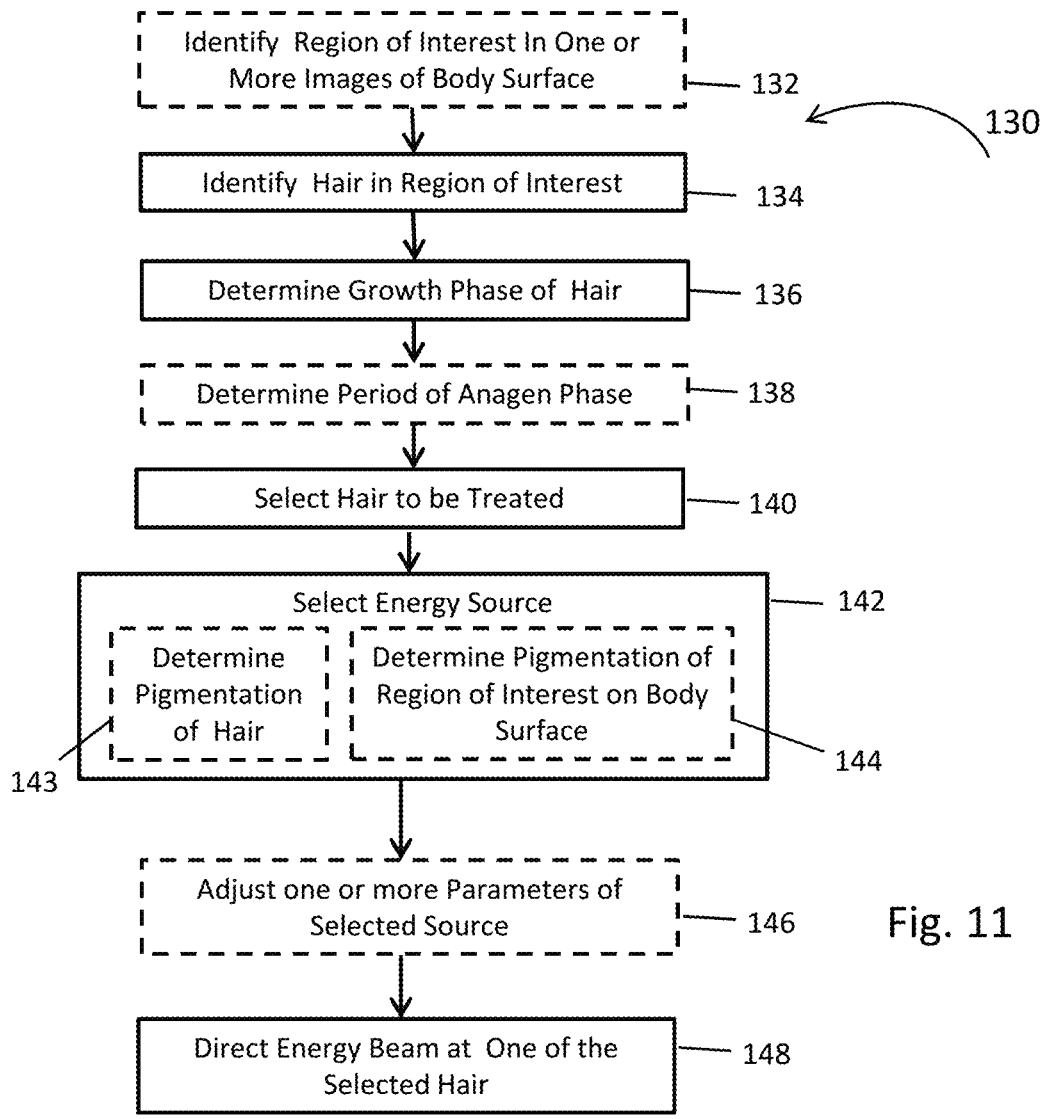
FIG. 11 is a flow diagram of an example of general methodology for automated hair removal according to some embodiments.

A general methodology of using the automated treatment system 25 to perform therapeutic or cosmetic procedure related to skin and hair according to the present disclosure is discussed in reference to FIG. 11. Using an example of hair removal or depilation, FIG. 11 illustrates a flow diagram for an improved method 130 for removing hair from a body surface, a method which maybe semi- or completely automated. The proposed improved methodology and the system configured to implement such methodology may also result in less painful and/or more efficient procedure for the patient and one that may take less time. In some embodiments, the proposed methodology automatically determines the hair growth phase of the hair follicles of interest and uses that information at least as one of the factors in selecting hair for removal during particular session of the treatment. It also uses that information to schedule the number of procedures needed as well as the timing interval between the procedures. While the example of FIG. 11 is discussed with reference to hair removal, it should be understood that the same general methodology may be used in other procedures and adjusted as needed for a particular treatment or application.

As a preliminary matter, one or more regions of interest on a body surface may be identified from one or more images that have been acquired, for example, regions from which it is desired that hair be removed, such as the upper section of a back of a patient or the lower portion of a leg of a patient. These one or more regions of interest may be identified through a user interface, manually by the operator, semi-automatically, or automatically by the system. For example, the operator may manually position the cameras to image a region of interest, the system may automatically identify a boundary of a region of interest (a leg, an arm etc.), or utilize fiducials to indicate one or more boundaries of a region of interest. This preliminary step 132 of the method is shown in broken lines to indicate that this step is optional to the methodology and may be performed separately. Once the region of interest is identified, the current methodology begins in step 134 with identifying all or some hairs in the region of interest, for example, using known image processing techniques, including but not limited to segmentation, edge detection and thresholding. Identifying hair follicles comprises identifying their location and orientation in a 3-D coordinate system (including angle with respect to the body surface and direction).

Having identified the hairs as stated above, a determination is made in step 136 as to the growth phase of the identified hairs in a region of interest. Determining which hairs are in which hair growth phase (and especially identifying hair in the anagen growth phase) is useful in planning hair removal according to this aspect of the disclosure. The determined hair growth phase may be used, for example, in combination with other factors to achieve successful outcome of the procedure. For example, the hair growth phase information may be used not only to select particular hair for depilation, but also to choose a timing of each hair removal session, to reduce the total number of sessions. The overall condition of the hair growth phases of the hair and the distribution of the hairs in different hair growth phases over various portions of the body surface at issue may be also used as an important treatment planning tool and a more successful outcome may be realized.

Figure 13:
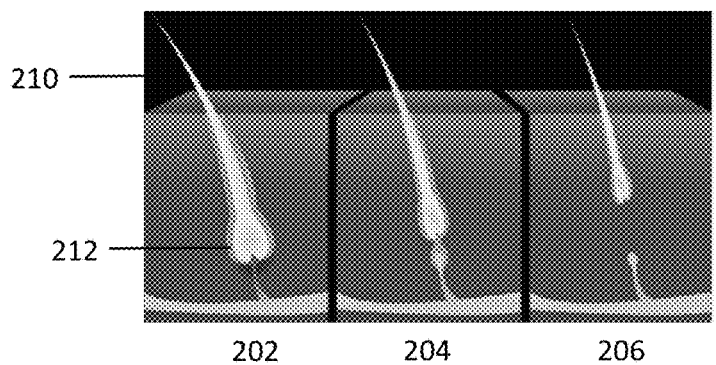
FIG. 13 illustrates a schematic of the phases of the hair growth.

Referring now to FIG. 13, various phases of hair growth are explained. There are three main phases of the hair growth cycle: anagen, catagen and telogen phases. The Anagen phase (202) is the first phase of the hair cycle during which new hair is growing and the hair follicle 210 is elongating. The hair bulb 212 is a bulb-shaped structure at the bottom part of the hair follicle. This is the living part of the hair. The bulb holds several types of stem cells that divide every 23 to 72 hours, faster than any other cells in the body. The bulb also contains hormones that affect hair growth. Stem cells at the hair bulb 212 nourish the hair and produce melanocytes, the cells that produce and store pigment in both hair and skin. This phase is responsible for determining the length of the hair shaft, with hair on the legs, under arms, and in the bikini area typically being in the anagen phase for a period of 4-6 weeks. Also, in the anagen phase, the hair is typically thicker/coarser than in the catagen or telogen phase, typically around 0.1 mm in thickness compared to about 0.05 mm (depending on various factors, such as age, gender, race/ethnicity, location of hair, nature of hair etc.). The hairs are long, and rich in melanin, with blond, red or white (grey) hair comprising pheomelanin, and brown or black hair comprising eumelanin. Approximately 75%-95% of hair follicles in the scalp of a healthy person are normally in the anagen phase. This hair cycle length and percentage may differ on other parts of the body, for example, the hair growth cycle for hair in the eyebrow hairs is typically 4-7 months.

Catagen (204) is the second phase of the hair cycle, a brief portion in the hair cycle when the hair growth stops and hair transitions to a resting period. This is a transitional phase which typically lasts 2-3 weeks and is characterized by apoptosis of the hair matrix cells and involution of the lower part of the follicle. During catagen phase, the hair bulb 212 migrates up from the hypodermis to the mid-dermis, the length of the hair shortens and the hair receives less nourishment from the stem cells, and therefore less pigmentation/color.

Telogen (206), the final phase, (resting phase) is the part of the hair cycle that follows the catagen phase. The hair receives no nourishment from the stem cells, and no pigmentation/color. During this phase hair shaft production is absent and the hair bulb is completely keratinized. The telogen phase, in the scalp follicles, lasts about 3 to 4 months but it is considerably longer in other body regions such as the lower limbs. The hair shaft remains anchored to the follicle during the telogen phase. Whereas hair in the anagen phase grows at approximately 0.35 mm per day (1 cm per month), telogen hair does not grow.

According to step 136 of the general methodology of FIG. 11, determination of the growth phase of the identified hair may comprise determining if hair is in the anagen phase or not. For example, a recipient of the hair removal procedure may be required to make an intial appointment in order for it to be determined which hair is in the anagen phase by various methodologies. The phase may be determined, for example, by its thickness or caliber, as explained above. However, there are other ways which may be adopted in the identification of anagen growth phase hair based on either pre-existing data of the recipient, pre-existing data from other recipients, or data collected via other reputable sources, otherwise referred to as historic or statistical data. This data may be characterized based on one or more of gender, age, race, ethnicity, patient history, patient medical history and/or the area of the body from which the hair is being removed. Optionally, or in addition, image data for the identified follicular units may be utilized to identify hair as being in the anagen growth phase, and the phase of hair growth may be determined simultaneously with identifying hair in the region, so that steps 134 and 136 may be performed together.

Since it is known that in the anagen phase, hair grows more than 0.25-0.45 mm per day, for example 0.33 mm per day, it can be assumed that hair that has not substantially grown is not in the anagen phase, but rather is in a telogen growth phase. Therefore, in one example, if a patient were to shave the area which were to have hair removed about three (3) days prior to their hair removal appointment, and at the appointment an image of the region shaved were taken, the anagen hair would be identified to be the hair that had grown about 1 mm over the 3 day period of time. Hairs that had not grown approximately the above amount could be considered to be hair in the catogen or telogen phase. In another example, such classification may be carried out automatically, for example, by a processor, based on one or more other characteristics of the phases of hair, as described above and also illustrated in FIG. 13. For example image processing above and/or below the body surface may enable data to be attained in connection with one or more of the thickness/caliber of the hair, the pigmentation/color associated with the hair shaft, the length of the hair shaft beneath the body surface, just to name few examples. In some embodiments, optionally, as shown in step 138 by a broken line, a sub-phase or a particular period of the anagen phase, typically a middle of the anagen phase, may be additionally identified. This sub-phase may be an optimal time for performing efficient hair removal because it may have the potential to optimize the heating potential of the hair when targeted by an activated energy delivery device. Alternatively, or in addition, in this optional step 138, a hair in a melanin-rich stage of the anagen growth phase may be identified.

Having determined which hairs of the population of hair in the regions of interest are in the anagen growth phase, in some embodiments, an indication of such may be relayed to the operator, on a display screen, for example. In one embodiment, a graphic representation may be assigned to the hair determined to be in the anagen growth phase, and that graphic representation may be overlayed on the corresponding hairs or otherwise displayed on the monitor. In step 140, the one or more hair follicles to be treated are selected. This selection may be performed automatically by the system, or optionally, the operator may provide input to the system, for example via a user interface, indicating whether the hairs that have been determined and visualized to be anagen hair should be subjected to depilation, and/or identifying additional hair follicles which may be added to hair removal treatment, or eliminating one or more of the determined anagen hair from being depilated. In some embodiments, the user may additionally indicate via the user interface the order in which the hair follicles determined to be in the anagen growth phase are removed from the body surface. In the automated implementations, the image processing unit may be configured (for example, programmed) to select for removal some or all of the hair follicles identified to be in the anagen growth phase, and optionally dictate the order of removal.

At this stage, the operator may also, in step 142, based on the provided information, select an appropriate energy delivery device to remove the determined anagen phase hair from the region of interest. Alternatively, in steps 142, the energy delivery device may be automatically selected by the system, based at least in part on the acquired image data. The energy delivery device or source may be selected for a particular individual hair follicle or, if appropriate and beneficial for efficiency, it may be selected for a group of hair follicles within a certain region. In this manner, a treatment plan is generated whereby only hair follicles determined to be in the anagen growth phase are targeted by the energy delivery device, such as a laser, and any additional appropriate selection parameters are considered for the final selection of hair for depilation. At the same time those hair follicles, which are not in the anagen growth phase are avoided.

Some recipients of laser hair removal procedures may want to have hair removed from various parts of the body surface, such as arms, back or legs. In order to ensure that the most appropriate energy device is selected (by either the operator or automatically by the system), among other things, such body surface differentiations may be taken into consideration. Optionally, in order to select the most appropriate energy delivery device or source, the pigmentation/color of the hair and/or the pigmentation/color of the region of interest of the body surface may be determined in steps 143 or 144, or both. Based on the pigmentation/color of the hair/skin, as explained earlier, some energy sources may be more suitable than others. Having selected the energy source in step 142, optionally in step 146, one or more parameters of the selected source may be adjusted before it is utilized to remove hair. The one or more parameters associated with the energy delivery device may comprise, for example, its frequency/wavelength of operation, spot size, activation time, pulse length, pulse duration and/or fluence. One of the parameters important when selecting a laser is the wavelength which dictates the depth of penetration that can be achieved. Other parameters include for example the pulse width/spot size. A larger spot size, or a larger physical width of the beam enables the beam to penetrate a larger number of follicles, and therefore provides for a shorter, less expensive treatment. A greater pulse width enables the heat that has been generated to be sustained for a longer period of time, thus providing a greater chance that the hair that is being targeted will be destroyed. Fluence is a metric of the density of energy applied, and a greater value provides greater heat, and therefore a greater chance of destroying the hair. However, the combination of frequency/wavelength, spot size, pulse duration and fluence may affect not only hair, but skin too, and selection of an appropriate energy source, as well as its associated parameters is important to the overall result achieved. In step 148, an energy beam of the selected energy delivery device or source is directed at and aligned/oriented relative to one of the selected hair. Directing and aligning/orienting the beam with the selected hair may be accomplished, for example, as described above in reference to FIG. 5, 5A or 5B. Once the selected hair follicle is treated, and when the same energy delivery device is selected for a number of hair follicles in the group, the selected energy delivery device is then directed and aimed at another hair follicle within the selected identified group, and repeated until all hair follicles within the group are treated. However, if the selected energy delivery device is only optimal for a particular hair follicle or a small group of hair follicles, then the step of selecting energy delivery device is repeated for other one or more hair follicles and such newly selected energy source or device is directed to the respective one or more hair follicles for which it was selected. Though energy delivery device selection may theoretically be carried out for each and every hair follicle consecutively, this would obviously be rather time consuming, and therefore, to the extent the same energy delivery device (and also the setting for the energy delivery device) may be used on a plurality of hair in the group, such approach will be more beneficial.

By utilizing one or more cameras to obtain images above and below the surface of the skin using light of different wavelengths, image processing, comprising for example subtraction and/or combination of images above the skin surface and below the skin surface, portions of the hair shaft of the follicular unit under the skin surface can be identified, thereby providing a more exact location which the laser may target. The processor may then communicate that information to the controller, which is configured to aim the laser relative to the follicular unit based, at least in part, on the results of the identification of the hair shaft portion under the skin surface. In some embodiments, the laser may additionally be aimed at the bulb of the follicular unit. By targeting substantially only these regions, and not the surrounding tissue, a substantially successful hair removal procedure can be achieved, with minimal damage to surrounding tissue, and more importantly for the recipient of the procedure, a reduction in the heating skin and therefore hopefully a corresponding reduction in discomfort or pain.

In some embodiments, the spot size of the energy delivery device, such as a laser beam, may be selected to be large enough to target and cover all melanin-rich parts of the hair follicle. In some embodiments the controller maneuvers the energy delivery device such that the spot size of the energy delivery device substantially maximizes an intersection between the laser beam, at least a portion of a hair shaft and at least a portion of a bulb of the identified hair in the anagen phase.

By targeting only these identified areas with an energy delivery device (such as a laser beam) with a specific wavelength for a specific length of time, sufficient energy may be absorbed, the targeted area becomes heated, essentially destroying the cells responsible for hair growth, and thereby inhibiting further growth of the hair, at least for a while. By not wasting time aiming energy (such as laser beams) at hairs which will not be affected by the beam, and not exposing unnecessary areas of the body surface such a laser beam when they do not need to be, the potential discomfort and/or pain experienced by the recipient of the procedure can be reduced. Depending upon the pricing adopted by the physician for the treatment, it is feasible that one or more of the reduction of time over which the laser is fired, the reduction of time over which the procedure is performed, and reduction of the time spent by the operator providing the treatment, may also potentially reduce the bottom line cost to the recipient of the procedure.

The determination to proceed with the procedure, as well as the proposed timing of the procedure, may be automatically proposed by the system (based, for example, on the pre-programmed information), or it may be selected by the user (physician) from the several options available through the user interface, or it may be chosen directly by the physician. In one embodiment, a determination may be made as to the best time for a patient to have a procedure, or the best time defined as the time which will most likely result in a successful procedure based on the proportion or percentage of hair in the area that is in the anagen growth phase. Hair that is subjected to laser energy during its anagen phase will have a higher chance of being removed, and therefore, aid in a successful hair removal session and achieving desired aesthetic outcome.

According to further aspect, a method for using analysis of hair growth phase to plan hair transplantation, may comprise: identifying one or more hair follicles within a predefined region on the body surface; determining a type of hair growth phase for the one or more hair follicles; determining a proportion of hair in the anagen hair growth phase; assigning a representation to and populating the predefined region with only those representations corresponding to hair in an anagen hair growth phase; and planning a hair transplant procedure based at least in part on the determined proportion of the anagen hair and/or on a distribution of the populated representation. Planning may comprise determining when to undergo a hair removal procedure. The representations may also aid in providing a metric, providing not only an indication of the proportion of hair in the anagen hair growth phase, but also their distribution throughout the predefined area. Such metrics may be utilized for example, to provide an indication of the length of the hair removal session, which will be based, for example, on the number of hairs that can be removed without causing unnecessary discomfort and/or pain. Such metrics may also be utilized to determine the number of sessions that may be required and how far apart such sessions will be scheduled based on the number and distribution of hair in the anagen phase. In other embodiments, the locations from where hair has been removed can be recorded and referred to in later appointments, thereby creating a specific record for a specific patient.

Figure 12:
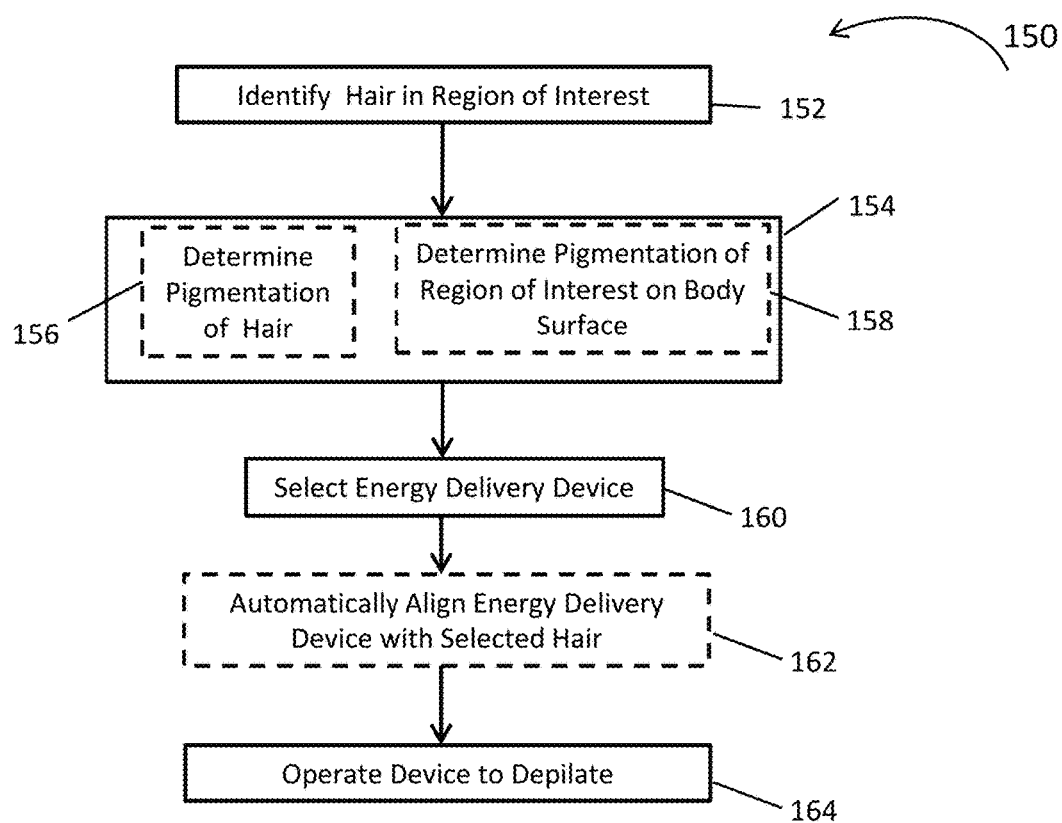
FIG. 12 is a flow diagram of another example of general methodology for automated hair removal according to some further embodiments.

Another example of a general methodology of hair depilation using an automated system according to some further embodiments is demonstrated in FIG. 12. As before, the method 150 starts with identifying plurality of unwanted hair follicles in a region of interest (step 152). This step may include identifying location and orientation of each unwanted hair follicle as previously discussed (including their 3-D coordinates). Step 154 may comprise one or both of the following: a) determining (for example, automatically measuring and assigning) color or pigmentation value(s) for some or all of the identified hair follicles (step 156) and determining (e.g., automatically measuring and assigning) color/pigmentation value(s) of a region of interest on a body surface (e.g., color of a skin or a portion of the skin) (step 158). In step 160 an energy delivery device may be selected, for example, as described in reference to FIG. 11. Optionally, in some embodiments, in step 162, the energy delivery device may be automatically directed to align with one of the identified hair follicles, for example, aligning with a general direction of a hair shaft of one of the identified hair follicles. This may be accomplished, for example, as explained in reference to FIG. 5, 5A or 5B. The beam of the energy delivery device may be aligned with the hair shaft portion of the hair follicle above the skin or with the anticipated direction of the below the surface portion of the hair shaft. The method may comprise a step of operating the energy delivery device to depilate one or more of the identified hair follicles.

According to yet another aspect, the automated treatment system 25, such as hair depilation device, may alternatively be configured to provide two or more different treatments in a region of interest. For example, a patient may desire to have a tattoo removed from his upper back region, which over the years has also become somewhat covered by hair, the operator may consider it beneficial to the patient that the hair be removed prior to the patient undergoing a tattoo removal procedure. According to this aspect of the disclosure, a single system 25 may be utilized for both procedures, potentially in the same treatment session. After acquiring the one or more images of the body surface comprising the tattoo, the system may automatically identify where the tattoo is located, and identify the hairs that may be disposed in the same area. Having done so, a determination of the growth phase of the hairs can be determined. Once the pigmentation of the hair in the anagen growth phase within the tattoo region has been determined, and a determination of the pigmentation of the region of interest (the area where the tattoo is) has been ascertained, the system may automatically select the appropriate energy sources to affect removal of the anagen growth phase hairs, and the tattoo, and adjust one or more of the frequency, spot size, pulse duration or fluence accordingly. In this instance however, before activating and directing the energy sources at the skin pigments to remove the tattoo, the selected energy source, such as a laser, may be activated and directed at the anagen growth phase hairs to remove the hairs. In this manner, when the energy sources or delivery devices are activated and directed at the skin pigments to remove the tattoo, there are no hairs to deal with, potentially providing for a less painful tattoo removal process. Other examples of situations in which two or more different treatments might be desired in a region of interest, include areas which may contain age spots, sun spots, acne scars, freckles, as well as unwanted hair.

It will be appreciated that a similar combination of energy sources may be selected such that the differing pigmentation in body surface due to tan lines, and differing pigmentation in hair due to sun exposure, for example, can be accommodated. In one configuration, the software incorporated into the controller may be configured to select the appropriate energy source in real-time, on a hair-by-hair basis or for a group of hair follicles, or all hair follicles in the area. In another configuration, the system may be configured to determine prior to the energy sources being activated one or any combination of the following: anagen hair, pigmentation of hair, pigmentation of body surface and melanin-rich areas within the hair follicle. The treatment plan may be provided such that all hair determined to require the activation of one energy source are treated prior to the second source being activated.

The system and apparatus of the present disclosure provides another improvement over existing hair depilation devices as it allows for an automated, effective and efficient cooling to protect tissue and reduce pain in a region of the body surface where depilation procedure is performed. Instead of a manual application of cryogen spray or taking pain medications, in some embodiments according to the present disclosure, cooling is achieved through the use of an air jet. The air jet, which may comprise one or more jets, may be provided on the moveable arm for directing an air stream at the body surface. The one or more jets may be configured such that the air emanating from them is automatically substantially aligned with the direction of the energy from the energy delivery device. In certain embodiments, the air jets may be automatically activated, directed and aligned according to the direction of the energy delivery device when it is being aligned with the hair follicles, as previously explained. In yet another embodiment, a user interface may be provided for a user to input instructions to one or both of the processor and controller regarding the timing as to when the air jet is activated (for example, having the air jet activated simultaneously with the energy delivery device), for how long for, at which location(s) and orientation(s). Additionally, rather than air jet, other cooling fluids may be utilized.

Figure 14:
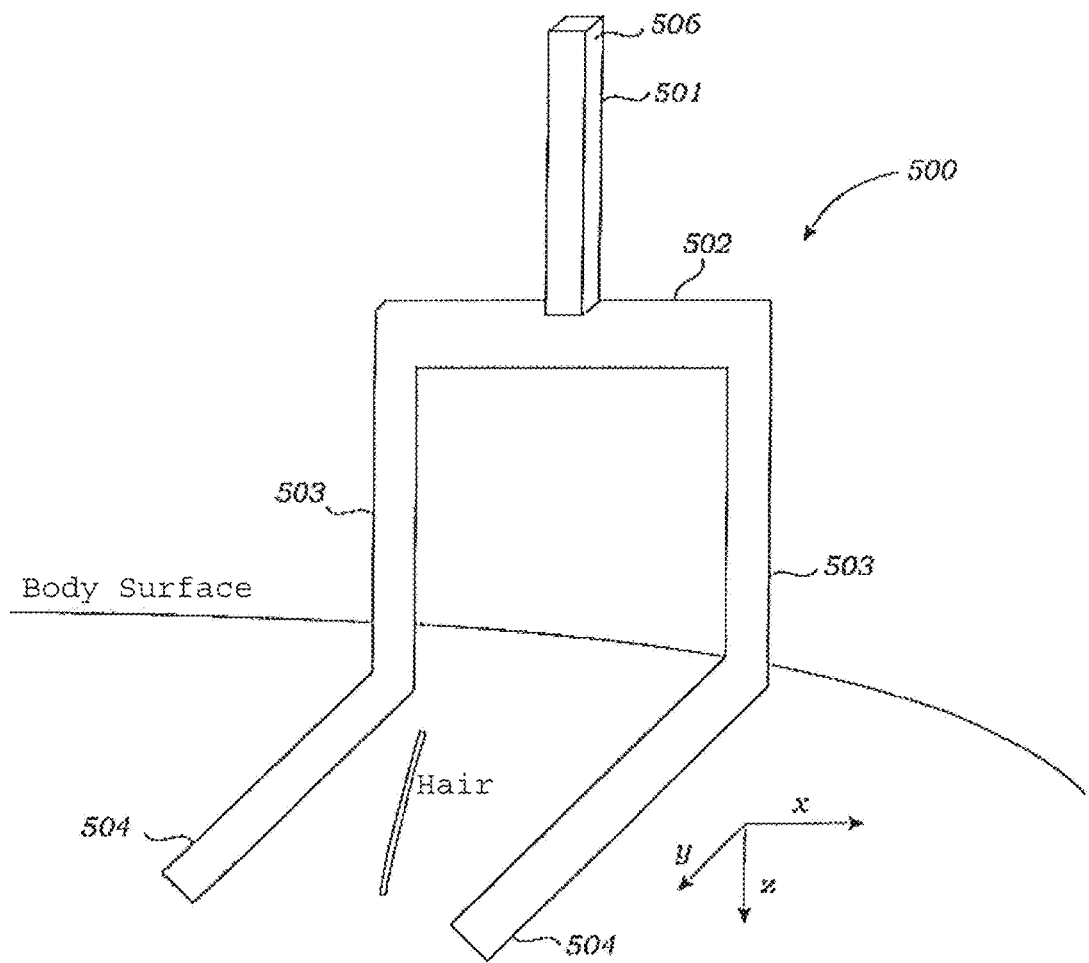
FIG. 14 illustrates an example of a skin tensioner that can be used with various embodiments described herein.

FIG. 14 illustrates an example of a skin tensioner 500 that may be used with embodiments described herein. The skin tensioner 500 includes a shaft 501, a horizontal support 502, and two side tines 503. Each tine 503 includes a distal portion 504 for pressing against a skin surface. The proximal end 506 of the shaft 501 is configured (e.g., sized and shaped) to engage with an end-effector of the robotic hair transplant system. The horizontal support 502 includes a spring-loaded mechanism (not shown) that exerts a force along the x-axis, thereby causing the tines 503 to spread apart from each other. During use, the distal portions 504 of the tines 503 are positioned next to a hair follicle or follicular unit, with the hair being between the two distal portions 504. The spring-loaded mechanism then spreads the tines 503 apart to thereby tension the skin. As a result, the hair shaft associated with the hair follicle may stand more erect relative to the scalp surface. The puncture needle and coring needle, or any other tool described herein, such as a laser beam, would act between the distal portions 504 of the tines 503. Other configuration of the skin tensioning device may be used with the system and methods of the present disclosure.

Moreover, although individual features of one embodiment may be discussed herein or shown in the drawings of the one embodiment and not in other embodiments, it should be apparent that individual features of one embodiment may be combined with one or more features of another embodiment or features from a plurality of embodiments. By way of non-limiting example, it will be appreciated by those skilled in the art that particular features or characteristics described in reference to one figure or embodiment may be combined as suitable with features or characteristics described in another figure or embodiment. Applicant regards the subject matter of the disclosure to include all combinations and sub-combinations of the various steps, elements, features, functions, and/or properties disclosed herein. It is to be understood that other embodiments than those described above may be utilized and structural or logical changes may be made without departing from the scope of the present disclosure. The Detailed Description, therefore, is not to be taken in a limiting sense. It will also be apparent that although the methodology described above as discrete steps, one or more steps may be combined or even deleted, without departing from the intended functionality of the embodiments.

The forgoing illustrated and described embodiments of the invention are susceptible to various modifications and alternative forms, and it should be understood that the invention generally, as well as the specific embodiments described herein, are not limited to the particular forms or methods disclosed, but to the contrary cover all modifications, equivalents and alternatives falling within the scope of the appended claims. By way of non-limiting example, it will be appreciated by those skilled in the art that the invention is not limited to the use of a robotic system, including a robotic arm, and that other automated and semi-automated systems that have a moveable arm assembly may be used for carrying and precisely positioning the respective camera(s) and tool assemblies adjacent the body surface.

What is claimed:

1. A method of hair depilation using an automated system, the method comprising:
   automatically identifying in an image acquired by an imaging device, a location and orientation of unwanted hair follicles in a region of a body surface;
   automatically measuring and assigning a hair pigmentation value for some or all of the identified unwanted hair follicles;
   automatically measuring and assigning a skin pigmentation value in the region of the body surface with the identified unwanted hair follicles;
   based on one or both of the assigned skin pigmentation value and the assigned hair pigmentation value of one or more identified unwanted hair follicles, automatically selecting an energy delivery device from a plurality of energy delivery devices operatively connected to the automated system; and
   based on the identified location and orientation of one of the one or more identified hair follicles, automatically directing the selected energy delivery device to position relative to a general direction of a hair shaft of the one of the one or more identified hair follicles.

2. The method of claim 1, comprising operating the energy delivery device to depilate the one of the one or more identified hair follicles.

3. The method of claim 1, wherein the step of automatically directing comprises aligning the energy delivery device with a general direction of a hair shaft or aligning the energy delivery device with a general direction of a beneath a skin portion of the hair shaft of the one of the one or more identified hair follicles.

4. The method of claim 1, wherein automatically selecting the energy delivery device is based on the assigned hair pigmentation values of a plurality of identified unwanted hair follicles.

5. The method of claim 1, comprising repeating the step of selecting the energy delivery device for each individual or a selected group of identified hair follicles.

6. The method of claim 1, comprising repeating the aligning step for each of the one or more identified hair follicles.

7. The method of claim 1, wherein automatically measuring and assigning a skin pigmentation value comprises analyzing a pre-existing data relating to skin pigmentation.

8. The method of claim 1, comprising identifying from the image acquired by the imaging device, among the some or all of the identified unwanted hair follicles, those hair follicles in an anagen hair growth phase.

9. The method of claim 8, wherein identifying those hair follicles in the anagen hair growth phase comprises determining corresponding calibers of the identified hair follicles.

10. An image-guided automated apparatus for hair depilation, comprising:
    an interface adapted to receive an image data containing images of a body surface; and
    a processor comprising a set of instructions for executing operation, the set of instructions including instructions for:
      automatically identifying in an image acquired by an imaging device, a location and orientation of unwanted hair follicles in a region of a body surface;
      automatically measuring and assigning a hair pigmentation value for some or all of the identified unwanted hair follicles;
      automatically measuring and assigning a skin pigmentation value in the region of the body surface with the identified unwanted hair follicles;
      based on one or both of the assigned skin pigmentation value and the assigned hair pigmentation value of one or more identified unwanted hair follicles, automatically selecting an energy delivery device from a plurality of energy delivery devices operatively connected to the automated system; and
      based on the identified location and orientation of one of the one or more identified hair follicles, automatically directing the selected energy delivery device to align with a general direction of a hair shaft of the one of the one or more identified hair follicles.

11. The image-guided automated apparatus of claim 10, wherein the apparatus is a robotic apparatus comprising a robotic arm and an energy delivery device coupled to the robotic arm.

12. The image-guided automated apparatus of claim 10, further comprising an air jet configured for directing an air stream at a targeted hair follicle.

13. The image-guided automated apparatus of claim 12, wherein the processor comprises instructions for automatically directing the air jet to align with the energy delivery device and activating the air jet simultaneously with activation of the energy delivery device.

14. The image-guided automated apparatus of claim 10, wherein said energy delivery device comprises a therapeutic laser or a cosmetic laser.

15. The image-guided automated apparatus of claim 10, wherein:
the apparatus comprises at least two lasers.

16. The image-guided automated apparatus of claim 10, wherein the processor is further configured to determine a time for which the selected energy delivery device is to be operated, based on a pigmentation of skin, and one or more of a pigmentation of an identified anagen hair and a caliber of an identified anagen hair.

17. The image-guided automated apparatus of claim 10, further comprising a display, and wherein an identified hair follicle determined to be in an anagen hair growth phase is assigned a representation, and an image of the region of interest is populated with the assigned representation for each of the identified anagen hair.

18. The image-guided automated apparatus of claim 17, wherein the processor comprises instructions for creating a hair removal plan based at least in part on one or both of the identified anagen hair follicles and a distribution of the anagen hair within the region of interest.

19. The image-guided automated apparatus of claim 10, comprising one or more cameras configured to obtain images above and below a surface of the skin using light of different wavelengths, and processing the images comprises subtraction and/or combination during image processing of the images above the skin surface and below the skin surface to identify a portion under the skin surface of the hair shaft of the follicular unit, and wherein the processor comprises instructions for aligning the energy delivery device with the hair shaft based, at least in part, on the results of the identification of the hair shaft portion under the skin surface.

20. The image-guided automated apparatus of claim 18, further comprising a module for determining a time interval between a current and a subsequent hair removal appointment based at least in part on one or both of a determined proportion of the anagen hair and a distribution of the anagen hair within the region.

21. The image-guided automated apparatus of claim 10, wherein automatically directing the selected energy delivery device comprises aligning the energy delivery device with a general direction of a portion of the hair shaft beneath a skin or orienting the energy delivery device at an offset angle to a general direction of a hair shaft portion above a skin of the one of the one or more identified hair follicles.

* * * * *